(12) United States Patent
Montgomery et al.

(10) Patent No.: US 11,839,471 B2
(45) Date of Patent: Dec. 12, 2023

(54) AUTOREGULATION MONITORING USING DEEP LEARNING

(71) Applicant: Covidien LP, Mansfield, MA (US)

(72) Inventors: Dean Montgomery, Edinburgh (GB); Paul S. Addison, Edinburgh (GB); Andre Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 255 days.

(21) Appl. No.: 17/210,222

(22) Filed: Mar. 23, 2021

(65) Prior Publication Data
US 2022/0304598 A1 Sep. 29, 2022

(51) Int. Cl.
*A61B 5/1455* (2006.01)
*A61B 5/00* (2006.01)

(52) U.S. Cl.
CPC ........ *A61B 5/14553* (2013.01); *A61B 5/7264* (2013.01)

(58) Field of Classification Search
CPC ..... A61B 5/031; A61B 5/02028; A61B 5/026; A61B 5/7267; A61B 5/7264; A61B 5/02007; A61B 5/4076; A61B 5/14553; A61B 5/021; A61B 5/14542; G06T 2207/30104; G06T 2207/30048; G16H 40/63; G16H 50/20; G16H 50/30; G16H 50/50; G16H 50/70

See application file for complete search history.

(56) References Cited

U.S. PATENT DOCUMENTS

| | | | |
|---|---|---|---|
| 5,743,267 A | 4/1998 | Nikolic et al. | |
| 6,599,251 B2 | 7/2003 | Chen et al. | |
| 6,689,069 B2 | 2/2004 | Bratteli et al. | |
| 7,070,566 B2 | 7/2006 | Medero et al. | |
| 7,927,283 B2 | 4/2011 | Riobo et al. | |
| 8,366,627 B2 | 2/2013 | Kashif et al. | |
| 8,702,604 B2 | 4/2014 | Karamanoglu et al. | |
| 9,474,451 B2 | 10/2016 | Brady et al. | |
| 9,861,317 B2 | 1/2018 | Ochs | |
| 10,542,923 B2 | 1/2020 | Chang et al. | |
| 10,595,790 B2 | 3/2020 | Itu et al. | |
| 10,660,530 B2 | 5/2020 | Montgomery et al. | |
| 10,740,638 B1* | 8/2020 | Annis | G06V 30/412 |
| 10,932,673 B2 | 3/2021 | Addison et al. | |
| 11,026,586 B2 | 6/2021 | Addison et al. | |

(Continued)

FOREIGN PATENT DOCUMENTS

WO 2017001023 A1 1/2017

OTHER PUBLICATIONS

Chuan et al., "Is Cerebrovascular Autoregulation Associated with Outcomes After Major Noncardiac Surgery? A Prospective Observational Pilot Study," Acta Anaesthesiologica Scandinavica, Jul. 11, 2018, 10 pp.

(Continued)

*Primary Examiner* — Eric F Winakur
*Assistant Examiner* — Elina Sohyun Ahn
(74) *Attorney, Agent, or Firm* — Fletcher Yoder, P.C.

(57) ABSTRACT

In some examples, a system is configured to determine, using a neural network algorithm of a cerebral autoregulation model, a cerebral autoregulation status of the patient based at least in part on a blood pressure of the patient over a period of time and regional cerebral oxygen saturation of the patient over the period of time.

18 Claims, 8 Drawing Sheets

(56) References Cited

U.S. PATENT DOCUMENTS

| | | | |
|---|---|---|---|
| 11,102,304 B1* | 8/2021 | Jain | H04L 67/63 |
| 2005/0015009 A1 | 1/2005 | Mourad et al. | |
| 2007/0293760 A1* | 12/2007 | Schaafsma | A61B 5/4884 |
| | | | 600/454 |
| 2009/0326386 A1 | 12/2009 | Sethi et al. | |
| 2011/0105912 A1 | 5/2011 | Widmar et al. | |
| 2011/0201911 A1 | 8/2011 | Johnson et al. | |
| 2015/0327779 A1 | 11/2015 | Breskin et al. | |
| 2016/0196384 A1 | 7/2016 | Mansi et al. | |
| 2016/0242700 A1 | 8/2016 | Ferber et al. | |
| 2016/0324425 A1* | 11/2016 | Addison | A61B 5/4064 |
| 2016/0367197 A1 | 12/2016 | Addison et al. | |
| 2017/0095161 A1 | 4/2017 | Addison et al. | |
| 2017/0105631 A1 | 4/2017 | Addison et al. | |
| 2017/0105671 A1 | 4/2017 | Borgos | |
| 2017/0196501 A1 | 7/2017 | Watson et al. | |
| 2018/0014791 A1 | 1/2018 | Montgomery et al. | |
| 2018/0020991 A1 | 1/2018 | Aung et al. | |
| 2018/0049649 A1 | 2/2018 | Addison et al. | |
| 2018/0070831 A1 | 3/2018 | Sutin et al. | |
| 2018/0110455 A1 | 4/2018 | Chang et al. | |
| 2018/0249916 A1 | 9/2018 | Bienek et al. | |
| 2018/0338731 A1 | 11/2018 | Addison et al. | |
| 2019/0328241 A1 | 10/2019 | Addison et al. | |
| 2020/0107763 A1 | 4/2020 | Antunes et al. | |
| 2020/0129076 A1 | 4/2020 | Montgomery et al. | |
| 2020/0146636 A1 | 5/2020 | Addison | |
| 2020/0187866 A1 | 6/2020 | Antunes et al. | |
| 2020/0251201 A1 | 8/2020 | Ilan | |
| 2021/0177275 A1 | 6/2021 | Addison et al. | |
| 2022/0213558 A1* | 7/2022 | Levin | G16H 50/20 |

OTHER PUBLICATIONS

Mohamadlou et al., "Prediction of Acute Kidney Injury with a Machine Learning Algorithm using Electronic Health Record Data," Canadian Journal of Kidney Health and Disease, vol. 5, Nov. 22, 2017, 9 pp.

Prough, MD, et al., "Monitoring the Brain to Save the Kidneys" Publication info: Critical Care Medicine, Feb. 2013, vol. 41, No. 2, pp. 671-673.

Scheeran et al., "Journal of Clinical Monitoring and Computing 2016 End of Year Summary: Monitoring Cerebral Oxygenation and Autoregulation," Springer Science and Business Media, Journal of Clinical Monitoring and Computing, vol. 31, Jan. 2017, pp. 241-246.

Tsalach et al., "Cerebral Autoregulation Real-Time Monitoring," PLoS One vol. 11, No. 8, Aug. 29, 2016, 27 pp.

U.S. Appl. No. 17/354,811, filed Jun. 22, 2021, naming inventors Montgomery et al.

Addison et al., "Gradient adjustment method for better discriminating correlating and non-correlating regions of physiological signals: application to the partitioning of impaired and intact zones of cerebral autoregulation", Journal of Clinical Monitoring and Computing, vol. 31, No. 04, Aug. 5, 2016, pp. 727-737.

International Search Report and Written Opinion of International Application No. PCT/US2022/071240 dated Jun. 21, 2022, 17 pp.

Malykhina et al., "Digitalization of medical services for detecting violations of cerebrovascular regulation based on a neural network signal analysis algorithm", Proceedings of the 2nd International Scientific Conference on Innovations in Digital Economy, Oct. 22, 2020, pp. 1-7.

* cited by examiner

AUTOREGULATION MONITORING USING DEEP LEARNING

TECHNICAL FIELD

This disclosure relates to monitoring autoregulation status of a patient.

BACKGROUND

Clinicians may monitor one or more physiological parameters of a patient, e.g., to monitor a patient's autoregulation status. Autoregulation is the response mechanism by which an organism regulates blood flow over a wide range of systemic blood pressure changes through complex myogenic, neurogenic, and metabolic mechanisms. During autoregulation, arterioles dilate or constrict in an attempt to maintain appropriate blood flow. Autoregulation may occur for a variety of organs and organ systems, such as, for example, the brain, the kidneys, the gastrointestinal tract, and the like. In the example of cerebral autoregulation, as cerebral blood pressure decreases, cerebral arterioles dilate in an attempt to maintain blood flow. As cerebral pressure increases, cerebral arterioles constrict to reduce the blood flow that could cause injury to the brain.

SUMMARY

This disclosure describes example devices, systems, and techniques for determining a cerebral autoregulation status of a patient using machine learning. For example, a system may be configured to receive a blood pressure signal indicative of a blood pressure of the patient over a period of time and an oxygen saturation signal indicative of a regional cerebral oxygen saturation of the patient over the period of time. The system may input the blood pressure of the patient and the regional cerebral oxygen saturation of the patient, as well as additional data associated with the patient, into a cerebral autoregulation model to determine the cerebral autoregulation model of the patient.

The cerebral autoregulation model may include a neural network algorithm that has been trained via machine learning training using training data from a population of patients. Such training data may include blood pressure data and regional cerebral oxygen saturation data of the population of patients along with labeled ground truths to enable the neural network algorithm to learn relationships between blood pressure and regional cerebral oxygen saturation of patients, and associations between such relationships and cerebral autoregulation statuses.

In some examples, the training data used to train the neural algorithm may also include additional data derived from the blood pressure data and regional cerebral oxygen saturation data, such as gradients of the blood pressure data, gradients of the regional cerebral oxygen saturation data, and cerebral oximetry indices that specify correlations between the blood pressure data and regional cerebral oxygen saturation data. Further, in some examples, the training data may also include additional data such as a bypass flag to indicate whether the patient was undergoing a cardiopulmonary bypass procedure.

By using a cerebral autoregulation model that includes a neural network algorithm that has been trained via machine learning training to determine the cerebral autoregulation status of patients, the techniques of this disclosure may enable cerebral autoregulation monitoring devices to more accurately determine the cerebral autoregulation status of patients with fewer false positives and false negatives compared with using rote algorithms that may be based only on blood pressure data of patients. As such, the techniques disclosed in this disclosure provides a technical advantage.

In one example, this disclosure describes a method that includes receiving a blood pressure signal indicative of a blood pressure of a patient over a period of time and an oxygen saturation signal indicative of a regional cerebral oxygen saturation of the patient over the period of time; determining, using a neural network algorithm of a cerebral autoregulation model, a cerebral autoregulation status of the patient based at least in part on blood pressure of the patient over the period of time and the regional cerebral oxygen saturation of the patient over the period of time; and sending, to an output device, a signal indicative of the cerebral autoregulation status of the patient.

In another example, this disclosure describes a system that includes a blood pressure sensing device; an oxygen saturation sensing device; and processing circuitry configured to: receive a blood pressure signal indicative of a blood pressure of a patient over a period of time from the blood pressure sensing device and an oxygen saturation signal indicative of a regional cerebral oxygen saturation of the patient over the period of time from the oxygen saturation sensing device; determine, using a neural network algorithm of a cerebral autoregulation model, a cerebral autoregulation status of the patient based at least in part on blood pressure of the patient over the period of time and the regional cerebral oxygen saturation of the patient over the period of time; and send, to an output device, a signal indicative of the cerebral autoregulation status of the patient.

In another example, this disclosure describes a non-transitory computer readable storable medium that includes instructions, that when executed by processing circuitry, cause the processing circuitry to receive a blood pressure signal indicative of a blood pressure of a patient over a period of time and an oxygen saturation signal indicative of a regional cerebral oxygen saturation of the patient over the period of time; determine, using a neural network algorithm of a cerebral autoregulation model, a cerebral autoregulation status of the patient based at least in part on blood pressure of the patient over the period of time and the regional cerebral oxygen saturation of the patient over the period of time; and send, to an output device, a signal indicative of the cerebral autoregulation status of the patient.

In another example, this disclosure describes an apparatus that includes means for receiving a blood pressure signal indicative of a blood pressure of a patient over a period of time and an oxygen saturation signal indicative of a regional cerebral oxygen saturation of the patient over the period of time; means for determining, using a neural network algorithm of a cerebral autoregulation model, a cerebral autoregulation status of the patient based at least in part on blood pressure of the patient over the period of time and the regional cerebral oxygen saturation of the patient over the period of time; and means for sending, to an output device, a signal indicative of the cerebral autoregulation status of the patient.

The details of one or more examples are set forth in the accompanying drawings and the description below. Other features, objects, and advantages will be apparent from the description and drawings, and from the claims.

DETAILED DESCRIPTION

Figure 1:
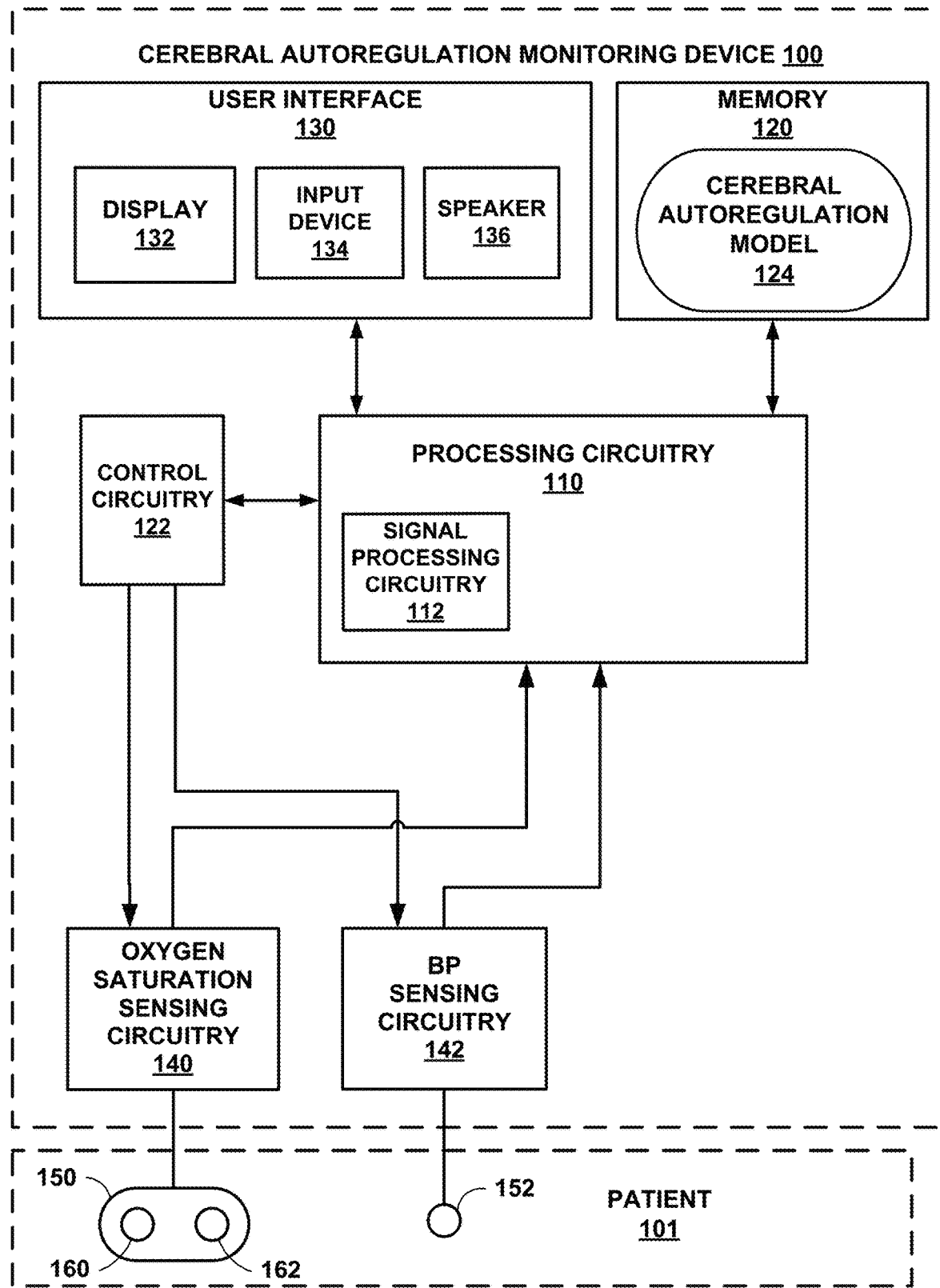
FIG. 1 is a conceptual block diagram illustrating an example cerebral autoregulation monitoring system.

FIG. 1 is a conceptual block diagram illustrating an example cerebral autoregulation monitoring system 100. As shown in FIG. 1, cerebral autoregulation monitoring system 100 includes processing circuitry 110, memory 120, control circuitry 122, user interface 130, sensing circuitry 140 and 142, and sensing devices 150 and 152. In the example shown in FIG. 1, user interface 130 may include display 132, input device 134, and/or speaker 136, which may be any suitable audio device configured to generate and output a noise and include any suitable circuitry. In some examples, autoregulation monitoring system 100 may be configured to determine and output (e.g., for display at display 132) the autoregulation status of a patient 101, e.g., during a medical procedure or for more long-term monitoring, such as in the intensive care unit (ICU) or for fetal monitoring. A clinician may receive information regarding the cerebral autoregulation status information of a patient via user interface 130 and adjust treatment or therapy to patient 101 based on the cerebral autoregulation status information.

When patient 101 exhibits an impaired autoregulation status, patient 101 may experience inappropriate blood flow, which may be undesirable. An autoregulation system of patient 101 may be impaired if the blood pressure gradient and the oxygen saturation gradient trend together (e.g., change in the same direction) over a period of time. An intact autoregulation status of patient 101 occurs over a range of blood pressures defined between a lower limit of autoregulation (LLA) and an upper limit of autoregulation (ULA). For example, below a lower limit of autoregulation (LLA), a drop in blood flow to a respective organ may cause ischemia and adversely affect the respective organ. Above an upper limit of autoregulation (ULA), an increase in blood flow to a respective organ may cause hyperemia, which may result in swelling or edema of the respective organ. A clinician may monitor the autoregulation status of a patient, e.g., during a medical procedure, and take one or more actions to keep the patient in or bring the patient to an intact autoregulation status, such as by increasing or decreasing the patient's blood pressure.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150 and 152. In some examples, control circuitry 122 may be configured to provide timing control signals to coordinate operation of sensing devices 150 and 152. For example, sensing circuitry 140 and 142 may receive from control circuitry 122 one or more timing control signals, which may be used by sensing circuitry 140 and 142 to turn on and off respective sensing devices 150 and 152, such as to periodically collect calibration data using sensing devices 150 and 152. In some examples, processing circuitry 110 may use the timing control signals to operate synchronously with sensing circuitry 140 and 142. For example, processing circuitry 110 may synchronize the operation of an analog-to-digital converter and a demultiplexer with sensing circuitry 140 and 142 based on the timing control signals.

Memory 120 may be configured to store, for example, monitored physiological parameter values of patient 101, such as blood pressure values, oxygen saturation values, regional cerebral oxygen saturation (rSO2) values, one or more cerebral autoregulation status values, one or more non-cerebral autoregulation status values, physiological parameters, mean arterial pressure (MAP) values, or any combination thereof. Memory 120 may also be configured to store data such as autoregulation state values including modified and unmodified values, threshold values and rates, smoothing functions, Gaussian filters, confidence metrics, expected autoregulation functions, historical patient blood pressure value data, and/or estimates of limits of autoregulation. The threshold values and rates, smoothing functions, Gaussian filters, confidence metrics, expected autoregulation functions, and historical patient blood pressure value data may stay constant throughout the use of device 100 and across multiple patients, or these values may change over time.

In some examples, memory 120 may store program instructions, such as neural network algorithms. The program instructions may include one or more program modules that are executable by processing circuitry 110. For example, memory 120 may store cerebral autoregulation model 124, which may be a model trained via machine learning to determine the cerebral autoregulation status of patient 101. When executed by processing circuitry 110, such program instructions, such as program instructions of cerebral autoregulation model 124, may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 may include a display 132, an input device 134, and a speaker 136. In some examples, user interface 130 may include fewer or additional components. User interface 130 is configured to present information to a user (e.g., a clinician). For example, user interface 130 and/or display 132 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, information about an autoregulation status (e.g., cerebral autoregulation status values and/or non-cerebral autoregulation status values), pulse rate information, respiration rate information, other patient physiological parameters, or combinations thereof via display 132. User interface 130 may also include circuitry and other components configured to generate and project an audio output to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joystick, a touch pad, or any other suitable input device or combination of input devices, an input signal. The input signal may contain information about patient 101, such as physiological parameters, treatments provided to patient 101, or the like. Additional input signals may be used by processing circuitry 110 in any of the determinations or operations it performs in accordance with processing circuitry 110.

In some examples, if processing circuitry 110 determines that the cerebral autoregulation status of patient 101 is impaired, then processing circuitry 110 may present a notification indicating the impairment. The notification may include a visual, audible, tactile, or somatosensory notification (e.g., an alarm signal) indicative of the cerebral autoregulation status of patient 101. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., a communication interface).

Oxygen saturation sensing circuitry 140 and blood pressure sensing circuitry (collectively, sensing circuitry 140 and 142) may be configured to receive physiological signals sensed by respective sensing devices 150 and 152 and communicate the physiological signals to processing circuitry 110. Sensing devices 150 and 152 may include any sensing hardware configured to sense a physiological parameter of a patient, such as, but not limited to, one or more electrodes, optical receivers, blood pressure cuffs, or the like. The sensed physiological signals may include signals indicative of physiological parameters of patient 101, such as, but not limited to, blood pressure, regional oxygen saturation, blood volume, heart rate, and respiration. For example, sensing circuitry 140 and 142 may include, but are not limited to, blood pressure sensing circuitry, oxygen saturation sensing circuitry, regional oxygen saturation sensing circuitry, regional cerebral oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof.

In some examples, sensing circuitry 140 and 142 and/or processing circuitry 110 may include signal processing circuitry 112 configured to perform any suitable analog conditioning of the sensed physiological signals. For example, sensing circuitry 140 and 142 may communicate to processing circuitry 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove dark or ambient contributions to the received signal. Additionally or alternatively, sensing circuitry 140 and 142 may include signal processing circuitry 112 to modify one or more raw signals and communicate to processing circuitry 110 one or more modified signals.

In some examples, oxygen saturation sensing device 150 is a regional oxygen saturation sensor configured to generate an oxygen saturation signal indicative of blood oxygen saturation within the venous, arterial, and/or capillary systems within a region of patient 101. For example, oxygen saturation sensing device 150 may be configured to be placed on the skin of patient 101, such as on patient 101's forehead, to determine regional oxygen saturation of a particular tissue region, e.g., the frontal cortex or another cerebral location of patient 101. Oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of light source 160. Light intensity of multiple wavelengths may be received at both the "close" and the "far" detector 162. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium).

In operation, light may enter detector 162 after passing through the tissue of patient 101, including skin, bone, other shallow tissue (e.g., non-cerebral tissue and shallow cerebral tissue), and/or deep tissue (e.g., deep cerebral tissue). Detector 162 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time. Such a technique described above may be referred to as near-infrared spectroscopy (NIRS), and the oxygen saturation signal may be referred to as a NIRS signal.

Oxygen saturation sensing device 150 may provide the oxygen saturation signal (e.g., regional oxygen saturation signal) to processing circuitry 110 or to any other suitable processing device to enable evaluation of an autoregulation status of patient 101. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation."

In operation, blood pressure sensing device 152 and oxygen saturation sensing device 150 may each be placed on the same or different parts of the body of patient 101. For example, blood pressure sensing device 152 and oxygen saturation sensing device 150 may be physically separate from each other and may be separately placed on patient 101. As another example, blood pressure sensing device 152 and oxygen saturation sensing device 150 may in some cases be part of the same sensor or supported by a single sensor housing. For example, blood pressure sensing device 152 and oxygen saturation sensing device 150 may be part of an integrated oximetry system configured to non-invasively measure blood pressure (e.g., based on time delays in a plethysmography (PPG) signal) and regional oxygen saturation. One or both of blood pressure sensing device 152 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example cerebral autoregulation monitoring system 100 is illustrated in FIG. 1, the components illustrated in FIG. 1 are not intended to be limiting. Additional or alternative components and/or implementations may be used in other examples.

Blood pressure sensing device 152 may be any sensor or device configured to generate a blood pressure signal indicative of a blood pressure of patient 101 at an acquisition site. For example, blood pressure sensing device 152 may include a blood pressure cuff configured to non-invasively monitor blood pressure, a sensor configured to noninvasively generate a PPG signal, or an arterial line for invasively monitoring blood pressure in an artery of patient 101. In some examples, the blood pressure signal may include at least a portion of a waveform of the acquisition blood pressure. In some examples, an acquisition site may include at least one of a femoral artery of patient 101, a radial artery of patient 101, a dorsalis pedis artery of patient 101, a brachial artery of patient 101, or combinations thereof. In some examples, blood pressure sensing device 152 may include a plurality of blood pressure sensing devices. For example, each blood pressure sensing device of the plurality of blood pressure sensing devices may be configured to obtain a respective blood pressure of patient 101 at a respective acquisition site of a plurality of acquisition sites. The plurality of acquisition sites may include similar or different arteries of patient 101.

In some examples, blood pressure sensing device 152 may include one or more pulse oximetry sensors. The acquisition blood pressure may be derived by processing time delays between two or more characteristic points within a single PPG signal obtained from a single pulse oximetry sensor. Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, entitled "Systems and Methods for Non-Invasive Blood Pressure Monitoring." In other cases, the blood pressure of patient 101 may be continuously, non-invasively monitored via multiple pulse oximetry sensors placed at multiple locations on patient 101. As described in commonly assigned U.S. Pat. No. 6,599,251, issued Jul. 29, 2003, entitled "Continuous Non-invasive Blood Pressure Monitoring Method and Apparatus," multiple PPG signals may be obtained from the multiple pulse oximetry sensors, and the PPG signals may be compared against one another to estimate the blood pressure of patient 101.

Regardless of its form, blood pressure sensing device 152 may be configured to generate a blood pressure signal indicative of a blood pressure of patient 101 (e.g., arterial blood pressure) over time. In examples in which blood pressure sensing device 152 includes a plurality of blood pressure sensing devices, the blood pressure signal may include a plurality of blood pressure signals, each indicative of a blood pressure of patient 101 at a respective acquisition site. Blood pressure sensing device 152 may provide the blood pressure signal to sensing circuitry 142, processing circuitry 110, or to any other suitable processing device to enable evaluation of the autoregulation status of patient 101.

In accordance with aspects of the present disclosure, processing circuitry 110 may be configured to receive a blood pressure signal generated by sensing circuitry 142 and sensing device 152 that is indicative of a blood pressure of patient 101 over a period of time and an oxygen saturation signal generated by sensing circuitry 140 and sensing device 150 that is indicative of a regional oxygen saturation of patient 101 over the period of time. The period of time over which processing circuitry 110 may be the previous 30 seconds, 60 seconds 90 seconds, 120 seconds, or any other suitable period of time.

The blood pressure signal that is indicative of a blood pressure of patient 101 over a period of time may indicate the mean arterial pressure (MAP) of patient 101, the average (i.e. mean) blood pressure in patient 101 during a single cardiac cycle. As such, in some examples, the blood pressure signal may indicate a MAP for each cardiac cycle of patient 101 during the period of time.

The regional oxygen saturation (rSO2) of patient 101 indicated by the oxygen saturation signal may be the regional oxygen saturation of the brain of patient 101. In some examples, oxygen saturation sensing device 150 may include multiple sensors that are placed on different parts of patient 101, such as a sensor placed on or near the right side of the head of patient 101, and a sensor placed on or near the left side of the head of patient 101. In this example, the oxygen saturation signal that is indicative of a regional oxygen saturation of patient 101 may include a first oxygen saturation signal from an oxygen saturation sensor placed on the right side of the head of patient 101 that is indicative of a first regional cerebral oxygen saturation of patient 101 and a second oxygen saturation signal from an oxygen saturation sensor placed on the left side of the head of patient 101 that is indicative of a second regional cerebral oxygen saturation of patient 101.

Processing circuitry 110 may be configured to determine physiological data associated with the blood pressure of patient 101 during the period of time and/or the regional oxygen saturation of patient 101 during the period of time based at least in part on received signals indicative of the blood pressure of patient 101 over the period of time and/or the regional oxygen saturation of patient 101. For example, processing circuitry 110 may determine a cerebral oximetry index (COx) of patient 101 during the period of time based at least in part on a linear correlation between the blood pressure of patient 101 and the regional oxygen saturation of patient 101 during the period of time. For example, processing circuitry 110 can determine the cerebral oximetry index from the correlation between cerebral oxygen saturation in the blood ($rSO_2$) and mean arterial pressure (MAP).

In some examples, processing circuitry 110 may determine the gradient of the MAP of patient 101 during the period of time, also referred to as a window, which may be the change in the MAP of patient 101 over the period of time. Processing circuitry 110 may also determine the gradient of the regional cerebral oxygen saturation of patient 101 during the period of time, which may be the change in the regional cerebral oxygen saturation of patient 101 over the period of time.

Processing circuitry 110 may be configured to determine, using cerebral autoregulation model 124, a cerebral autoregulation status of patient 101 based at least in part on the blood pressure of patient 101 during the period of time and the regional oxygen saturation of patient 101 during the period of time. As described in further detail throughout this disclosure, cerebral autoregulation model 124 may include a neural network algorithm trained via machine learning to determine the cerebral autoregulation status of patient 101. Processing circuitry 110 may execute cerebral autoregulation model 124 and may use the MAP of patient 101 during the period of time and the regional oxygen saturation of patient 101 during the period of time as inputs to cerebral autoregulation model 124 to generate an output from cerebral autoregulation model 124 that is indicative of the cerebral autoregulation status of patient 101.

In some examples, processing circuitry 110 may also input, into cerebral autoregulation model 124, additional information associated with the blood pressure of patient 101 during the period of time and/or the regional oxygen saturation of patient 101 during the period of time to determine the cerebral autoregulation status of patient 101 based on the additional information. For example, processing circuitry 110 may input one or more of: the gradient of the blood pressure (e.g., MAP) of patient 101 during the period of time, the gradient of the regional cerebral oxygen saturation of patient 101 during the period of time, the COx of patient 101 during the period of time, or a bypass flag indicative that patient 101 was undergoing a cardiopulmonary bypass procedure during the period of time.

In some examples, if processing circuitry 110 receives an oxygen saturation signal in the form of a NIRS signal, then processing circuitry 110 may input the raw NIRS signal indicative of the regional cerebral oxygen saturation of patient 101 into cerebral autoregulation model 124. In some examples, if processing circuitry 110 receives an oxygen saturation signal that includes a first oxygen saturation signal from an oxygen saturation sensor placed on the right side of the head of patient 101 that is indicative of a first regional cerebral oxygen saturation of patient 101 and a second oxygen saturation signal from an oxygen saturation sensor placed on the left side of the head that is indicative of a second regional cerebral oxygen saturation of patient 101, then processing circuitry 110 may input both the first and second regional cerebral oxygen saturation signals into cerebral autoregulation model 124. For example, processing circuitry 110 may input the two separate values into cerebral autoregulation model 124 or may input an average of the two values into cerebral autoregulation model 124. In some examples, processing circuitry 110 may also input the blood oxygen saturation (SpO2) of patient 101 into cerebral autoregulation model 124.

In some examples, processing circuitry 110 may also input, into cerebral autoregulation model 124, additional information regarding patient 101 and determine the cerebral autoregulation status of patient 101 based on the additional information. For example, such additional information may include morphology characteristics associated with the blood pressure of patient 101 during the period of time and/or morphology characteristics associated with the regional oxygen saturation of patient 101 during the period of time. The additional information may also include blood pressures of patient 101 during the period of time other than the MAP, such as the systolic blood pressure or diastolic blood pressure of patient 101 during the period of time. The additional information may also include patient demographic data regarding patient 101, such as the patient's age, the patient's age, information regarding patient 101's diet and lifestyle (e.g., whether patient 101 is a smoker), and the like. The cerebral autoregulation status of patients may differ based on the variables indicated by the additional information.

Processing circuitry 110 may be configured to execute cerebral autoregulation model 124 to output, based on the information inputted into cerebral autoregulation model 124, an indication of a cerebral autoregulation status of patient 101. For example, cerebral autoregulation model 124 may output a value indicative of whether the cerebral autoregulation status of patient 101 is one of: intact, impaired, or unknown. An intact cerebral autoregulation status may indicate the cerebral autoregulation control mechanism of patient 101 is functioning properly, whereas an impaired cerebral autoregulation status may indicate the cerebral autoregulation control mechanism of patient 101 is not functioning properly. Intact cerebral autoregulation function occurs over a range of blood pressures defined between a LLA and a ULA. The determination of the cerebral autoregulation status using of cerebral autoregulation model 124 may enable processing circuitry 110 to quickly determine the cerebral autoregulation function of patient 101, e.g., prior to or without having to determine the LLA and the ULA specific to patient 101.

In some examples, cerebral autoregulation model 124 is a neural network algorithm trained via machine learning to take a plurality of signals, including a blood pressure signal indicative of the blood pressure of patient 101 and an oxygen saturation signal indicative of the regional oxygen saturation of patient 101 as inputs to determine the cerebral autoregulation status of patient 101.

A neural network algorithm, or artificial neural network, may include a trainable or adaptive algorithm utilizing nodes that define rules. For example, a respective node of a plurality of nodes may utilize a function, such as a non-linear function or if-then rules, to generate an output based on an input. A respective node of the plurality of nodes may be connected to one or more different nodes of the plurality of nodes along an edge, such that the output of the respective node includes the input of the different node. The functions may include parameters that may be determined or adjusted using a training set of inputs and desired outputs, such as, for example, a predetermined association between a plurality of signals or values, such as a blood pressure signal or blood pressure value(s) from patient 101 or a population of patients and an oxygen saturation signal or oxygen saturation value(s) of patient 101 or a population of patients measured contemporaneously with the blood pressure signal, along with a learning rule, such as a back-propagation learning rule. The back-propagation learning rule may utilize one or more error measurement comparing the desired output to the output produced by the neural network algorithm to train the neural network algorithm by varying the parameters to minimize the one or more error measurements.

An example neural network includes a plurality of nodes, at least some of the nodes having node parameters. An input including at least the oxygen saturation signal generated by oxygen saturation sensing device 150 or oxygen saturation sensing circuitry 140 and indicative of a regional cerebral oxygen saturation of patient 101 over a period of time and the blood pressure signal generated by blood pressure sensing device 152 or blood pressure sensing circuitry 142 and indicative of a blood pressure of patient 101 over the period of time may be provided (input) to a first node of the neural network algorithm. In some examples, the input may include a plurality of inputs, each input into a respective node. The first node may include a function configured to determine an output based on the input and one or more adjustable node parameters. In some examples, the neural network may include a propagation function configured to determine an input to a subsequent node based on the output of a preceding node and a bias value. In some examples, a learning rule may be configured to modify one or more node parameters to produce a favored output. For example, the favored output may be constrained by one or more threshold values and/or to minimize one or more error measurements. The favored output may include an output of a single node, a set of nodes, or the plurality of nodes.

The neural network algorithm may iteratively modify the node parameters until the output includes the favored output. In this way, processing circuitry 110 may be configured to iteratively evaluating outputs of the neural network algorithm and iteratively modifying at least one of the node parameters based on the evaluation of the outputs of the neural network algorithm to determine the cerebral autoregulation status of a patient, such as patient 101, based on the modified neural network algorithm.

In some examples, processing circuitry 110, using cerebral autoregulation model 124, may determine the cerebral autoregulation status of patient 101 by determining a first value associated with a confidence of the cerebral autoregulation status of patient 101 being intact and a second value associated with a confidence of cerebral autoregulation status of patient 101 being impaired. Processing circuitry 110 may therefore execute cerebral autoregulation model 124 to determine, based at least in part on the first value associated with the confidence of the cerebral autoregulation status of patient 101 being intact and the second value associated with the confidence of the cerebral autoregulation status of patient 101 being impaired, the cerebral autoregulation status of patient 101.

For example, processing circuitry 110, using cerebral autoregulation model 124, may determine, a numerical value between 0 and 1 for each of the first value and the second value. If cerebral autoregulation model 124 indicates that the first value is greater than the second value, then cerebral autoregulation model 124 may output a value indicative of the cerebral autoregulation status of patient 101 as being intact. Conversely, if cerebral autoregulation model 124 determines that the second value is greater than the first value, then cerebral autoregulation model 124 may output a value indicative of the cerebral autoregulation status of patient 101 as being impaired. For example, if cerebral autoregulation model 124 determines that the value associated with a confidence of the cerebral autoregulation status of patient 101 being intact is 0.8 and that the value associated with a confidence of the cerebral autoregulation status of patient 101 being impaired, then cerebral autoregulation model 124 may output a value indicative of the cerebral autoregulation status of patient 101 as being intact.

In some examples, if cerebral autoregulation model 124 does not have enough confidence in classifying the cerebral autoregulation status of patient 101 as being either intact or impaired, then cerebral autoregulation model 124 may output a value indicative of the cerebral autoregulation status of patient 101 as being unknown. In some examples, if the difference between the value associated with the confidence of the cerebral autoregulation status of patient 101 being intact and the value associated with the confidence of the cerebral autoregulation status of patient 101 being impaired is less than or equal to a threshold value, cerebral autoregulation model 124 may output a value indicative of the cerebral autoregulation status of patient 101 as being unknown. For example, if the value associated with the confidence of the cerebral autoregulation status of patient 101 being intact is 0.6, the value associated with the confidence of the cerebral autoregulation status of patient 101 being impaired is 0.4, and the threshold value is 0.2, the cerebral autoregulation model 124 may output a value indicative of the cerebral autoregulation status of patient 101 as being unknown.

In some examples, cerebral autoregulation model 124 may perform post processing of values determined by cerebral autoregulation model 124 to determine the cerebral autoregulation status of patient 101. For example, cerebral autoregulation model 124 may average the value associated with the confidence of the cerebral autoregulation status of patient 101 being intact with previously determined values associated with the confidence of the cerebral autoregulation status of patient 101 being intact at the same blood pressure as the current blood pressure of patient 101. Similarly, cerebral autoregulation model 124 may average the value associated with the confidence of the cerebral autoregulation status of patient 101 being impaired with previously determined values associated with the confidence of the cerebral autoregulation status of patient 101 being impaired at the same blood pressure as the current blood pressure of the patient 101. That is, when cerebral autoregulation model 124 determines values associated with the confidence of the cerebral autoregulation status of patient 101 being intact and the confidence of the cerebral autoregulation status of patient 101 being impaired, these values may be associated with the blood pressure of patient 101 at the time these values were determined, and processing circuitry 110 may store an association of the blood pressure of patient 101 and the confidence values in memory 120.

In some examples, when cerebral autoregulation model 124 determines values associated with the confidence of the cerebral autoregulation status of patient 101 being intact and the confidence of the cerebral autoregulation status of patient 101 being impaired at a given blood pressure of patient 101, cerebral autoregulation model 124 may look up the confidence values stored in memory 120 associated with the same blood pressure. Cerebral autoregulation model 124 may average the value associated with the confidence of the cerebral autoregulation status of patient 101 being intact with previously determined values associated with the confidence of the cerebral autoregulation status of patient 101 being intact at the same blood pressure as the current blood pressure of patient 101, and may average the value associated with the confidence of the cerebral autoregulation status of patient 101 being impaired with previously determined values associated with the confidence of the cerebral autoregulation status of patient 101 being impaired at the same blood pressure as the current blood pressure of patient 101.

Cerebral autoregulation model 124 may therefore compare the averaged value associated with the confidence of the cerebral autoregulation status of patient 101 being intact and the averaged value associated with the confidence of the cerebral autoregulation status of patient 101 being impaired to determine the cerebral autoregulation status of patient 101. If cerebral autoregulation model 124 determines that the averaged value associated with the confidence of the cerebral autoregulation status of patient 101 being intact is greater than or equal to the averaged value associated with the confidence of the cerebral autoregulation status of patient 101 being impaired, and if the difference between the two values are greater than a threshold value, then cerebral autoregulation model 124 may determine that the cerebral autoregulation status of patient 101 is intact. If cerebral autoregulation model 124 determines that the averaged value associated with the confidence of the cerebral autoregulation status of patient 101 being impaired is greater than or equal to the averaged value associated with the confidence of the cerebral autoregulation status of patient 101 being intact, and if the difference between the two values are greater than a threshold value, then cerebral autoregulation model 124 may determine that the cerebral autoregulation status of patient 101 is impaired. If the difference between the two averaged values is less than or equal to the threshold value, then cerebral autoregulation model 124 may determine that the cerebral autoregulation status of patient 101 is unknown.

Once processing circuitry 110 has determined the cerebral autoregulation status of patient 101, processing circuitry 110 may generate and output information indicative of the cerebral autoregulation status of patient 101 to an output device, e.g., user interface 130. Processing circuitry 110 delivers the information to user interface 130. In some examples, the information may enable user interface 130, for example, display 132, speaker 136, and/or separate display(s) (not shown), to present a graphical user interface that includes information indicative of cerebral autoregulation status of patient 101, such as a cerebral autoregulation status value and/or an indication of an impaired autoregulation state of the brain. In some examples, the indication of autoregulation status may include text, colors, and/or audio presented to a user. Processing circuitry 110 may be further configured to present an indication of one or more cerebral autoregulation status values, one or more limits of autoregulation (e.g., LLA and/or ULA), blood pressure(s), oxygen saturation(s), or the like, on the graphical user interface. In addition to or instead of the graphical user interface, processor circuitry 110 may be configured to generate and present information indicative of a determined cerebral autoregulation status of patient 101 via speaker 136. For example, in response to detecting an impaired cerebral autoregulation state of patient 101, processing circuitry 110 may generate an audible alert via speaker 136.

In some examples, cerebral autoregulation monitoring system 100, e.g., processing circuitry 110 or user interface 130, may include a communication interface to enable cerebral autoregulation monitoring system 100 to exchange information with external devices. The communication interface may include any suitable hardware, software, or both, which may allow cerebral autoregulation monitoring system 100 to communicate with electronic circuitry, a device, a network, a server or other workstations, a display, or any combination thereof. For example, processing circuitry 110 may receive blood pressure values, oxygen saturation values, or predetermined data, such as predetermined cerebral autoregulation status values, predetermined non-cerebral autoregulation status value, or predetermined adjustment values from an external device via the communication interface.

The components of cerebral autoregulation monitoring system 100 that are illustrated and described as separate components are illustrated and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of cerebral autoregulation monitoring system 100 illustrated and described herein may be divided over multiple components. For example, some or all of the functionality of control circuitry 122 may be performed in processing circuitry 110, or sensing circuitry 140 and 142. In other examples, the functionality of one or more of the components may be performed in a different order or may not be required.

Figure 2:
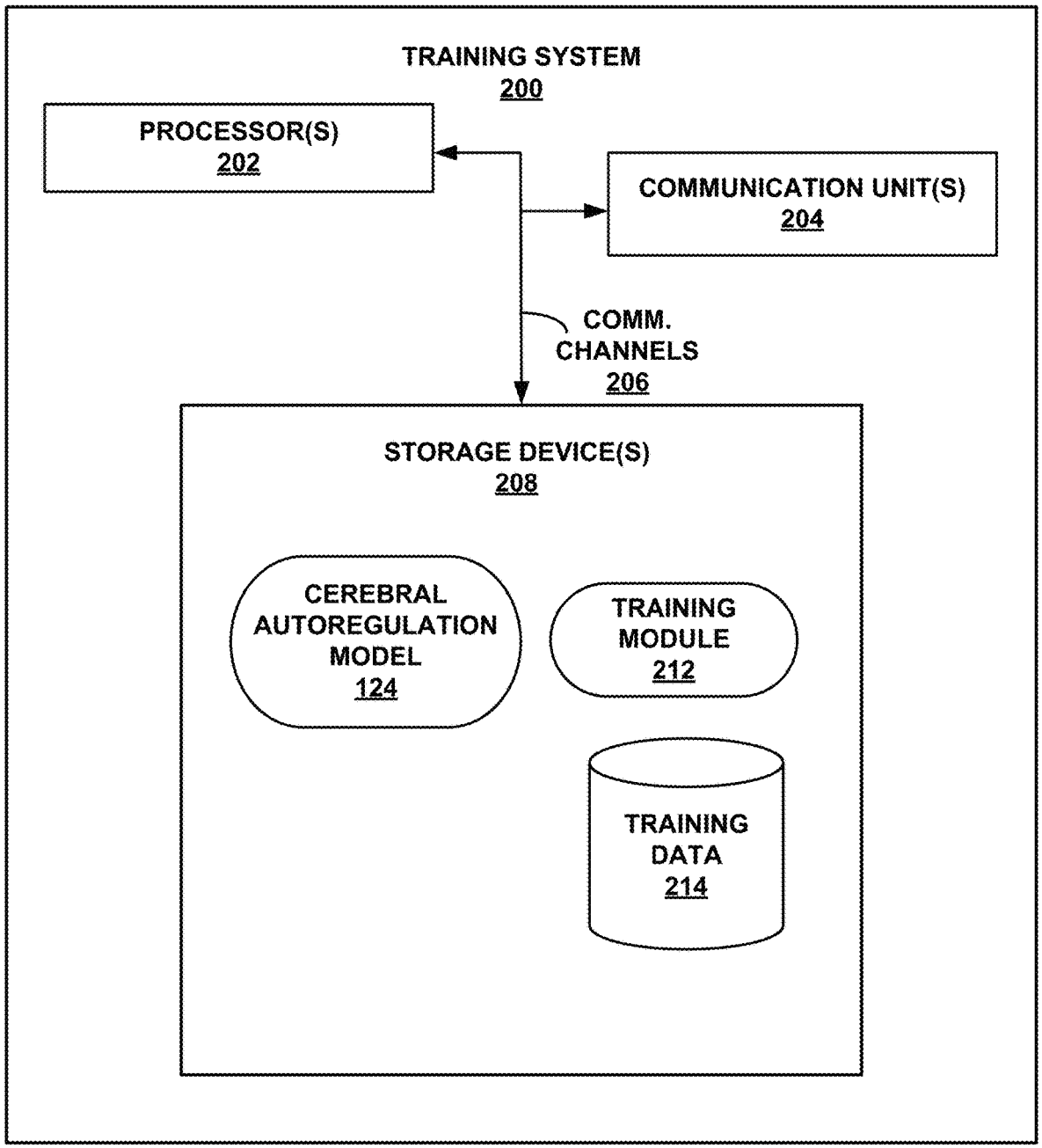
FIG. 2 illustrates details of an example training system that may perform training of the cerebral autoregulation model shown in FIG. 1.

FIG. 2 illustrates details of an example training system 200 that may perform training of cerebral autoregulation model 124 shown in FIG. 1. FIG. 2 illustrates only one particular example of training system 200, and many other example devices having more, fewer, or different components may also be configurable to perform operations in accordance with techniques of the present disclosure.

While displayed as part of a single device in the example of FIG. 2, components of training system 200 may, in some examples, be located within and/or be a part of different devices. For instance, in some examples, training system 200 may represent a "cloud" computing system. Thus, in these examples, the modules illustrated in FIG. 2 may span across multiple computing devices. In some examples, training system 200 may represent one of a plurality of servers making up a server cluster for a "cloud" computing system. In other examples, training system 200 may be an example of the cerebral autoregulation device 100 shown in FIG. 1.

As shown in the example of FIG. 2, training system 200 includes one or more processors 202, one or more communications units 204, and one or more storage devices 208. Storage devices 208 further include cerebral autoregulation model 124, training module 212, and training data 214. Each of components 202, 204, and 208 may be interconnected (physically, communicatively, and/or operatively) for inter-component communications. In the example of FIG. 2, components 202, 204, and 208 may be coupled by one or more communications channels 206. In some examples, communications channels 206 may include a system bus, network connection, inter-process communication data structure, or any other channel for communicating data. Cerebral autoregulation model 124, training module 212, and training data 214 may also communicate information with one another as well as with other components in training system 200.

In the example of FIG. 2, one or more processors 202 (each including processing circuitry) may implement functionality and/or execute instructions within training system 200. For example, one or more processors 202 may receive and execute instructions stored by storage devices 208 that execute the functionality of training module 212. These instructions executed by one or more processors 202 may cause training system 200 to store information within storage devices 208 during execution. One or more processors 202 may execute instructions of training module 212 to train cerebral autoregulation model 124 using training data 214. That is, training module 212 may be operable by one or more processors 202 to perform various actions or functions of training system 200 described herein.

In the example of FIG. 2, one or more communication units 204 may be operable to communicate with external devices (e.g., device 100 of FIG. 1) via one or more networks by transmitting and/or receiving network signals on the one or more networks. For example, training system 200 may use communication units 204 to transmit and/or receive radio signals on a radio network such as a cellular radio network. Likewise, communication units 204 may transmit and/or receive satellite signals on a satellite network such as a global positioning system (GPS) network. Examples of communication units 204 include a network interface card (e.g. such as an Ethernet card), an optical transceiver, a radio frequency transceiver, or any other type of device that can send and/or receive information. Other examples of communication units 204 may include Near-Field Communications (NFC) units, Bluetooth® radios, short wave radios, cellular data radios, wireless network (e.g., Wi-Fi®) radios, as well as universal serial bus (USB) controllers.

One or more storage devices 208 may be operable, in the example of FIG. 2, to store information for processing during operation of training system 200. In some examples, storage devices 208 may represent temporary memory, meaning that a primary purpose of storage devices 208 is not long-term storage. For instance, storage devices 208 of training system 200 may be volatile memory, configured for short-term storage of information, and therefore not retain stored contents if powered off. Examples of volatile memories include random access memories (RAM), dynamic random access memories (DRAM), static random access memories (SRAM), and other forms of volatile memories known in the art.

Storage devices 208, in some examples, also represent one or more computer-readable storage media. That is, storage devices 208 may be configured to store larger amounts of information than a temporary memory. For instance, storage devices 46 may include non-volatile memory that retains information through power on/off cycles. Examples of non-volatile memories include magnetic hard discs, optical discs, floppy discs, flash memories, or forms of electrically programmable memories (EPROM) or electrically erasable and programmable (EEPROM) memories. In any case, storage devices 208 may, in the example of FIG. 2, store program instructions and/or data associated with cerebral autoregulation model 124, training module 212, and training data 214.

Training system 200 may, in the example of FIG. 2, execute training module 212 to train cerebral autoregulation model 124 using training data 214 to more accurately and/or more quickly determine the cerebral autoregulation status of a patient by training cerebral autoregulation model 124 to associate one or more features with the cerebral autoregulation status of the patient. Cerebral autoregulation model 124 may include a deep learning architecture such as a recurrent neural network, convolutional neural network, and the like that includes multiple layers to progressively extract higher level features from inputs to cerebral autoregulation model 124.

In some examples, training module 212 trains cerebral autoregulation model 124 to use, as inputs, the blood pressure of a patient, such as the MAP of the patient, and regional cerebral oxygen saturation of the patient, and to determine, based on the MAP and the regional cerebral oxygen saturation of the patient, a cerebral autoregulation status (e.g., whether the cerebral autoregulation status is intact, impaired, or unknown) for the patient. Specifically, training module 212 trains cerebral autoregulation model 124 to use inputs such as the MAP and the regional cerebral oxygen saturation of a patient during a period of time to determine, based on the inputs during the period of time, the cerebral autoregulation status of the patient immediately following the period of time. Thus, if the period of time is 30 seconds, then training module 212 may train cerebral autoregulation model 124 to determine, based on inputs such as the MAP of the patient and regional cerebral oxygen saturation of the patient over a 30 second time period, the cerebral autoregulation status of the patient immediately following the 30 second time period.

For example, training module 212 may train cerebral autoregulation model 124 by providing data such as the MAP and the regional cerebral oxygen saturation over hours, days, and the like, and may train cerebral autoregulation model 124 by providing a truth label to label points in time in the data to indicate the cerebral autoregulation status as either intact or impaired. For example, if training module 212 is training cerebral autoregulation model 124 to determine, based on the inputs during a period of time of 30 seconds, the cerebral autoregulation status of the patient immediately following the period of time, training module 212 may label the data at 30 seconds to indicate a cerebral autoregulation status associated with the data (e.g., the MAP and the regional cerebral oxygen saturation) from time 0 to 30 seconds, label the data at 31 seconds to indicate a cerebral autoregulation status associated with the data from time 1 to 31 seconds, label the data at 32 seconds to indicate a cerebral autoregulation status associated with the data from time 2 to 32 seconds, and the like.

In some examples, training module 212 may train cerebral autoregulation model 124 by subtracting the mean value of the MAP from the MAP of the patient and by subtracting the mean regional cerebral oxygen saturation from the regional oxygen saturation of the patient. For example, for the time period from 0 to 30 seconds, training module 212 may subtract the mean value of the MAP over the entire training data from the MAP during the period of time from 0 to 30 seconds, and may subtract the mean value of the regional cerebral oxygen saturation over the entire training data from the regional oxygen saturation during the period of time from 0 to 30 seconds, and may use the resulting values as inputs to train cerebral autoregulation model 124.

Subtracting the mean value of the MAP from the MAP of the patient and by subtracting the mean regional cerebral oxygen saturation from the regional oxygen saturation of the patient may help to prevent the trained neural network in cerebral autoregulation model 124 from overfitting based on the absolute value of the MAP, such as to prevent cerebral autoregulation model 124 from being trained to learn that a MAP of less than 50 is usually associated with an impaired cerebral autoregulation status. Instead, training module 212 may train cerebral autoregulation model 124 to determine the cerebral autoregulation status of patients based on the relationship between trends in the MAP and trends in the regional cerebral oxygen saturation during the time period.

In addition to the MAP and the regional cerebral oxygen saturation, training module 212 trains cerebral autoregulation model 124 to use, as inputs, data in each time period such as, but not limited to, one more of: the gradient of the MAP during the time period (e.g., as a time series), the gradient of the regional cerebral oxygen saturation during the time period (e.g., as a time series), the cerebral oximetry index during the time period, a flag that indicates whether the patient is undergoing a medical procedure that may impact blood pressure values (e.g., cardiopulmonary bypass procedure) during the time period, the raw NIRS signal indicative of the regional cerebral oxygen saturation during the time period, oxygen saturation signals from oxygen saturation sensors placed on the left and right side of patients' heads, either as two separate signals or as a combined (e.g., averaged) signal, morphology characteristics associated with the blood pressure during the time period and/or morphology characteristics associated with the regional oxygen saturation during the time period, hemodynamic-related signals such as the systolic blood pressure or diastolic blood pressure during the time period, demographic data associated with patients, or the like.

In some examples, training module 212 trains cerebral autoregulation model 124 to also use, as inputs, the blood oxygen saturation (SpO2) of patients. Using the blood oxygen saturation of patients to train autoregulation model 124 may allow cerebral autoregulation model 124 to cope with changes in regional cerebral oxygen saturation due to changes in the blood oxygen saturation unrelated to cerebral blood flow. For example, training module 212 may train cerebral autoregulation model 124 to learn that changes in regional cerebral oxygen saturation due to changes in the blood oxygen saturation unrelated to cerebral blood flow is not necessarily a sign of a change in autoregulation status of a patient.

In some examples, training data 214 used to train cerebral autoregulation model 124 includes data from only patient 101 and from no other subjects. In other examples, training data 214 may include data from a population of patients that may or may not include patient 101. In some examples, once training module 212 has trained cerebral autoregulation model 124 using training data 214, training module 212 may test cerebral autoregulation model 124 by using a set of test data not yet encountered by using cerebral autoregulation model 124 to determine how closely the classification of cerebral autoregulation status by cerebral autoregulation model 124 based on the test data matches the expected cerebral autoregulation status classification of the test data. In this way, training module 212 may evaluate and further refine cerebral autoregulation model 124.

When training module 212 has completed training of cerebral autoregulation model 124, cerebral autoregulation model 124 can be installed, uploaded, or otherwise transferred to autoregulation monitoring system 100. In some examples, training module 212 may upload or otherwise transfer a copy of cerebral autoregulation model 124 to another server or to the cloud, and autoregulation monitoring system 100 may cerebral autoregulation model 124 via a network such as the Internet, a virtual private network, a local area network, and the like.

In some examples, training module 212 may be able to train cerebral autoregulation model 124 to determine the autoregulation status of organs besides the brain, such as the autoregulation status of kidneys, the gastrointestinal tract, and the like. In particular, training module 212 may use, in addition to regional cerebral oxygen saturation data, additional signals from these other organs as training data 214 to train cerebral autoregulation model 124 to determine the autoregulation status of organs besides the brain. Physiological parameters from which autoregulation status of a non-cerebral organ may be more directly determine can be relatively difficult to measure. Thus, determining an autoregulation status of a non-cerebral organ based on a cerebral autoregulation status value can be useful, e.g., as described in U.S. Pat. No. 10,932,673, entitled, "NON-CEREBRAL ORGAN AUTOREGULATION STATUS DETERMINATION," naming inventors Addison et al., and issued on Mar. 2, 2021. U.S. Pat. No. 10,932,673 is incorporated herein by reference in its entirety.

Figure 3:
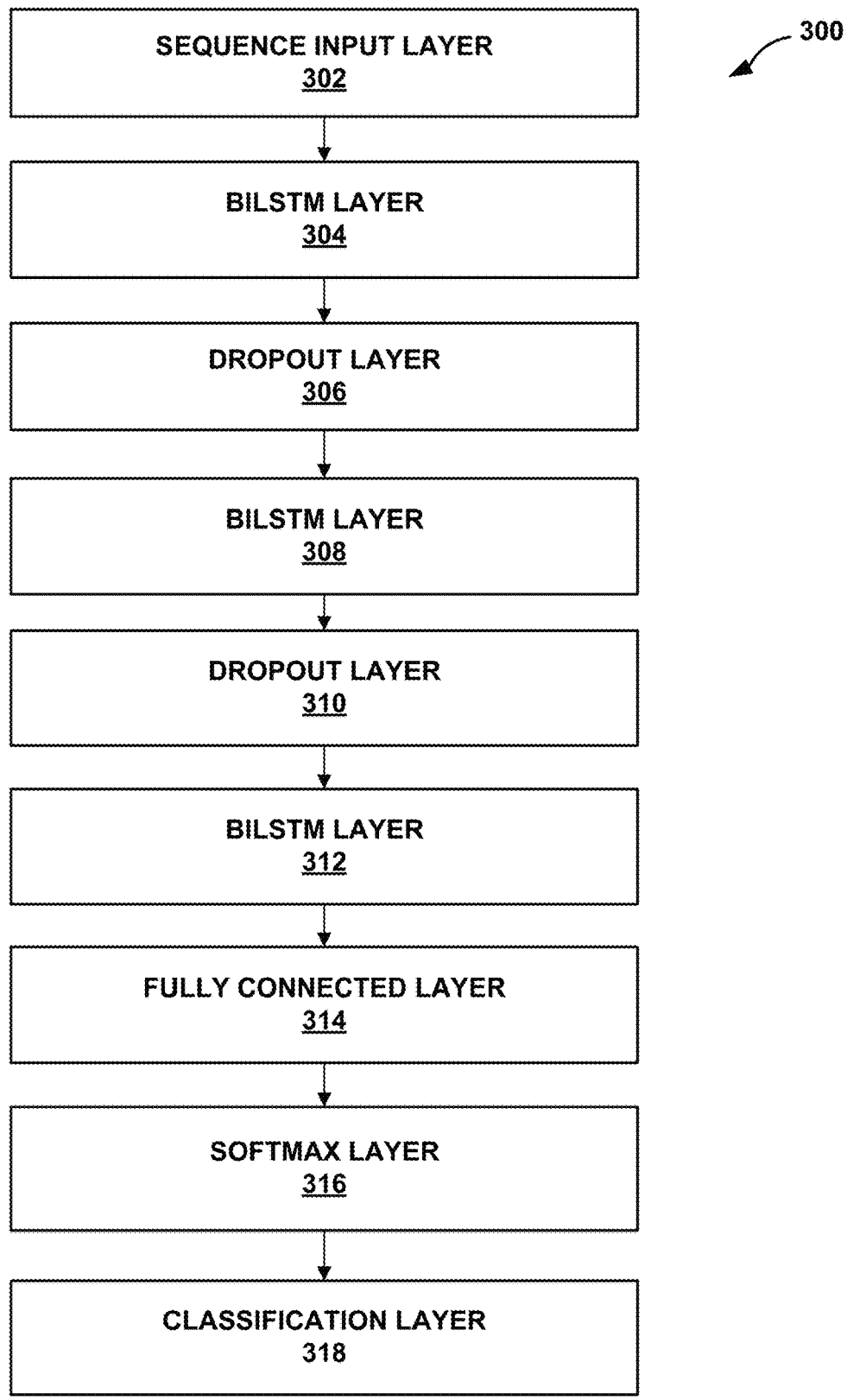
FIG. 3 illustrates an example deep learning architecture of the example cerebral autoregulation model of FIGS. 1 and 2.

FIG. 3 illustrates an example deep learning architecture 300 of the example cerebral autoregulation model 124 of FIGS. 1 and 2. While deep learning architecture 300 is illustrated in FIG. 3 as being a long short-term memory (LSTM) deep learning architecture that is used to train a LSTM model, any other deep learning architectures may equally be suitable for training cerebral autoregulation model 124.

As shown in FIG. 3, deep learning architecture 300 may include sequence input layer 302, bidirectional long short-term memory (BiLSTM) layer 304, dropout layer 306, BiLSTM layer 308, dropout layer 310, BiLSTM layer 312, fully connected layer 314, softmax layer 316 and classification layer 318. Sequence input layer 302 may be connected to BiLSTM layer 304. BiLSTM layer 304 may have 16 hidden units and may be connected to dropout layer 306. Dropout layer 306 may have a dropout ratio of 0.01 and may be connected to BiLSTM layer 308. BiLSTM layer 308 may have 8 hidden units and may be connected to dropout layer 310. Dropout layer 310 may have a dropout ratio of 0.01 and may be connected to BiLSTM layer 312. BiLSTM layer 312 may have 4 hidden units and may be connected to fully connected layer 314. Fully connected layer 314 may be connected to softmax layer 316. Softmax layer 316 may be connected to classification layer 318.

A sequence input layer such as sequence input layer 302 inputs sequence data to a neural network. Thus, sequence input layer 302 receives features that are used to train deep learning architecture 300, such as the MAP and the regional cerebral oxygen saturation of one or more patients over time.

A dropout layer such as dropout layers 306 and 310 randomly sets input elements to zero with a given probability. By randomly setting input elements to zero, a dropout layer may enable elements to be ignored during the training phase. Selectively ignoring elements during the training phase may prevent over-fitting of training data.

A BiLSTM layer such as BiLSTM layers 304, 308, and 312 learns bidirectional long-term dependencies between time steps of time series or sequence data. These dependencies may be useful for the network to learn from a complete time series at each time step.

A fully connected layer such as fully connected layer 314 multiplies the input (e.g., from BiLSTM layer 312) by a weight matrix and then adds a bias vector. A softmax layer, such as softmax layer 316 applies a softmax function to the input (e.g., from fully connected layer 314). The softmax function may be used as the last activation function of the neural network classifier (e.g., cerebral autoregulation model 124) to normalize the output of fully connected layer 314 to a probability of predicted output classes.

A classification layer such as classification layer 318 uses the probabilities of predicted output classes outputted by softmax layer 316 for the inputs to deep learning architecture 300 to assign the inputs to one of two or more mutually exclusive classes, and may output the output class of the inputs to cerebral autoregulation model 124 as a result of training cerebral autoregulation model 124 having deep learning architecture 300.

Figure 4:
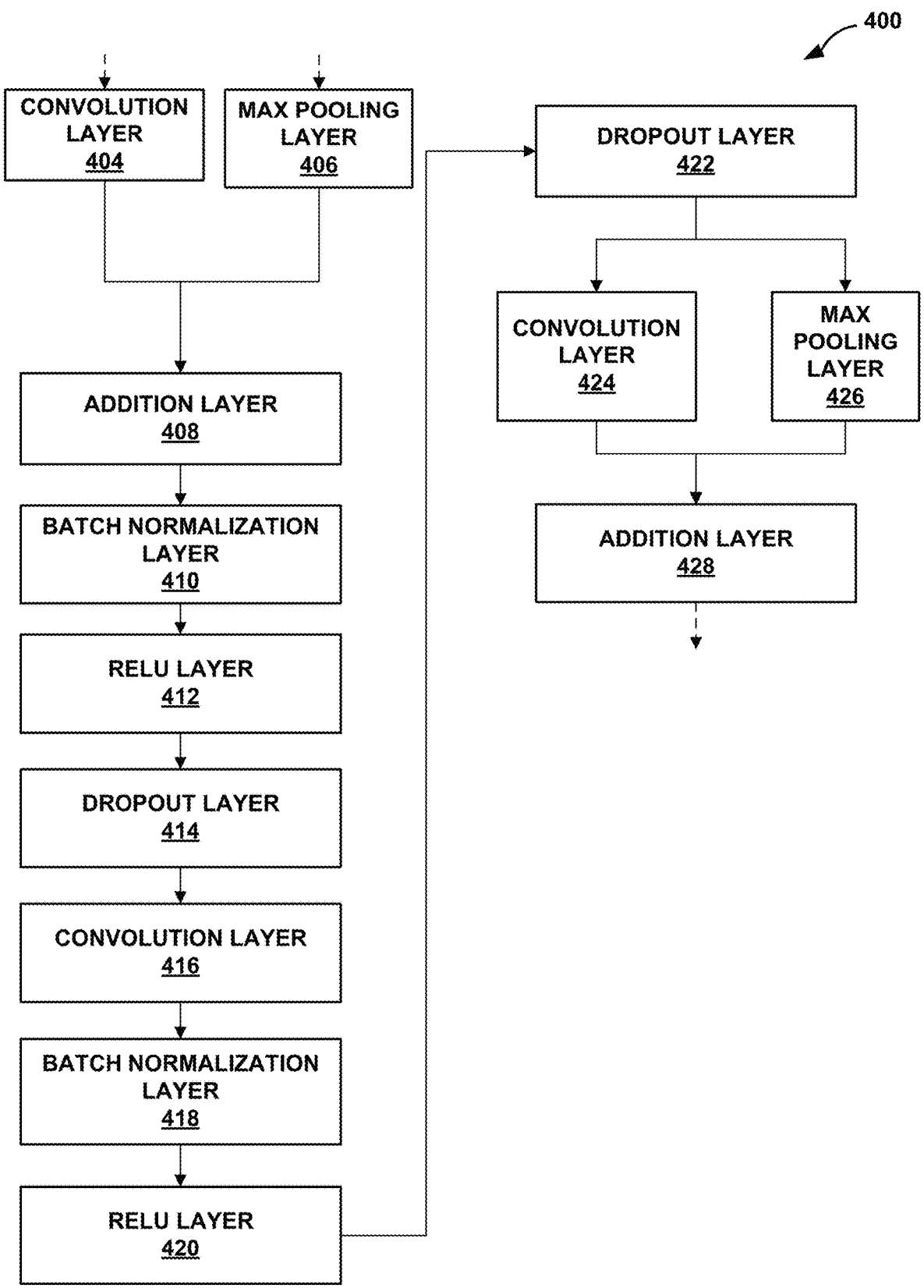
FIG. 4 illustrates an example deep learning architecture of the example cerebral autoregulation model of FIGS. 1 and 2.

FIG. 4 illustrates an example deep learning architecture 400 of the example cerebral autoregulation model 124 of FIGS. 1 and 2. While deep learning architecture 400 is illustrated in FIG. 4 as being a convolutional neural network (CNN) that is used to train a CNN model, any other deep learning architectures may equally be suitable for training cerebral autoregulation model 124.

As shown in FIG. 4, a portion of deep learning architecture 400 includes convolution layer 404, max pooling layer 406, addition layer 408, batch normalization layer 410, rectified linear unit (ReLU) layer 412, dropout layer 414, convolution layer 416, batch normalization layer 418, ReLU layer 420, dropout layer 422, convolution layer 424, max pooling layer 426, and addition layer 428. The portion of deep learning architecture 400 illustrated in FIG. 4 may be just a portion (i.e., less than all) of the hidden layers of the CNN that is deep learning architecture 400, and deep learning architecture may include other additional layers not shown in FIG. 4.

A two-dimensional convolution layer, such as convolution layers 404, 416, and 424 applies sliding convolutional filters to the input of the layer. The layer convolves the input by moving the filters along the input vertically and horizontally and computing the dot product of the weights and the input, and then adding a bias term.

A max pooling layer, such as max pooling layers 406 and 426, performs down-sampling by dividing the input into rectangular pooling regions and computing the maximum of each region. A max pooling layer follows convolutional layers for down-sampling, thereby reducing the number of connections to layers that follow the max pooling layer and reduces the number of parameters to be learned in the layers following the max pooling layer. A max pooling layer may also reduce overfitting in the neural network model.

An addition layer, such as addition layers 408 and 428, adds inputs from multiple neural network layers element-wise. In the example of deep learning architecture 400, addition layer 408 may add inputs from convolution layer 404 and max pooling layer 406, and addition layer 428 may add inputs from convolution layer 424 and max pooling layer 426.

A batch normalization layer, such as batch normalization layers 410 and 418, normalizes each input channel across a mini-batch. The batch normalization layer may speed up training of CNNs and reduce sensitivity to network initialization. A batch normalization layer can be used between convolutional layers and ReLU layers, so that batch normalization layer 410 is used in deep learning architecture 400 between convolution layer 404 and ReLU layer 412, and batch normalization layer 418 is used between convolution layer 416 and ReLU layer 420.

A ReLU layer such as ReLU layers 412 and 420, performs a threshold operation to each element of the input, where any value less than zero is set to zero. A ReLU layer may allow faster and more effective training of deep learning architecture 400 on large and complex datasets.

A dropout layer, such as dropout layers 414 and 422, randomly sets input elements to zero with a given probability. By randomly setting input elements to zero, a dropout layer may enable elements to be ignored during the training phase. Selectively ignoring elements during the training phase may prevent over-fitting of training data.

Figure 5:
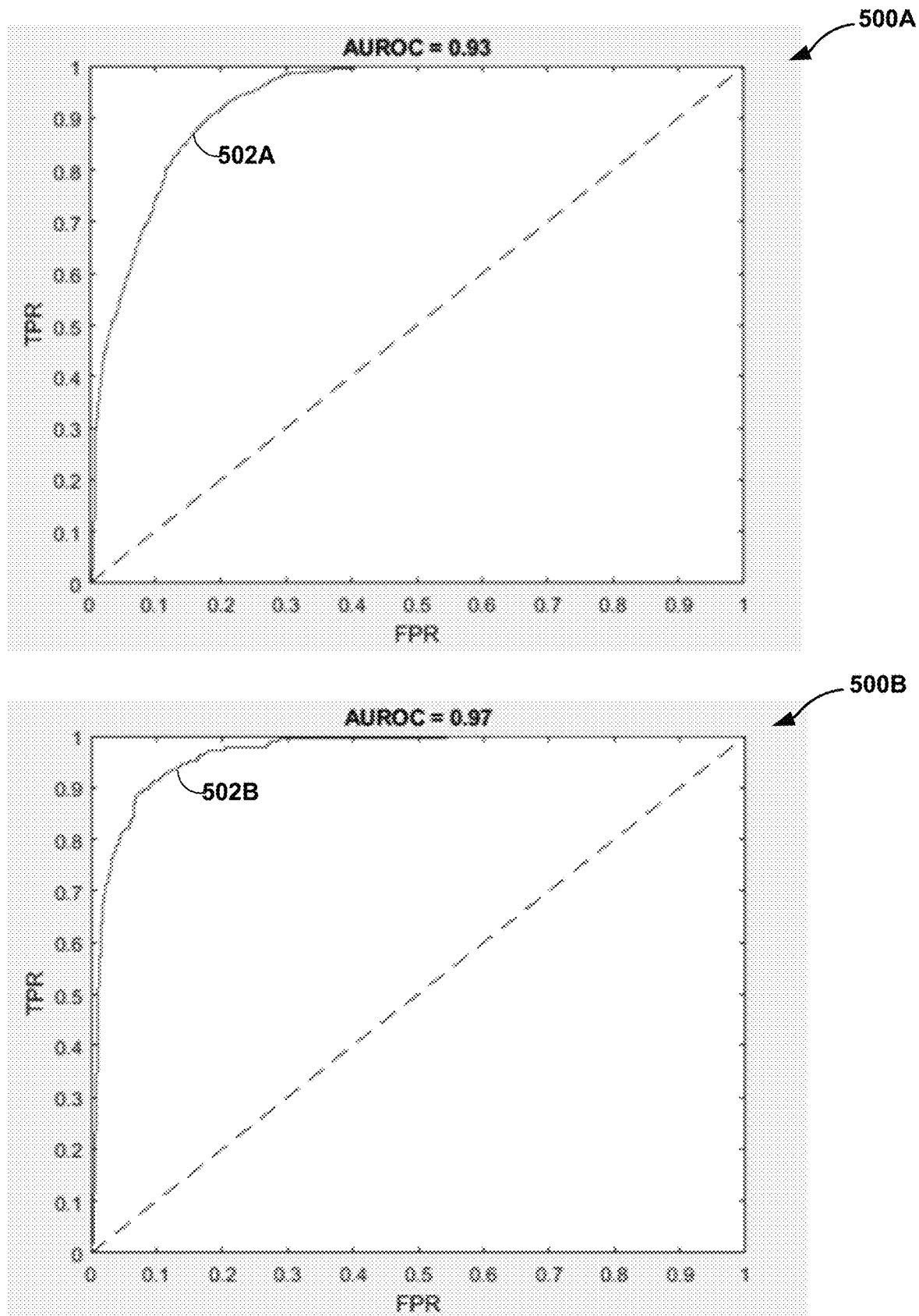
FIG. 5 illustrates example graphs of cerebral autoregulation status classification results using the deep learning architectures of FIGS. 3 and 4.

FIG. 5 illustrates example graphs of cerebral autoregulation status classification results using the deep learning architectures of FIGS. 3 and 4. As shown in FIG. 5, graph 500A illustrates the cerebral autoregulation status classification results using the LSTM deep learning architecture 300 of FIG. 3, and graph 500B illustrates the cerebral autoregulation status classification results using the CNN deep learning architecture 400 of FIG. 4.

Each of graphs 500A and 500B illustrates a receiver operating characteristic (ROC) curve, which is a graphical plot that illustrates the diagnostic ability of a binary classifier system as its discrimination threshold is varied. The y-axis of each of graphs 500A and 500B is the true positive rate (TPR) of cerebral autoregulation model 124 classifying cerebral autoregulation status, and the y-axis of each of graphs 500A and 500B is the false positive rate (FPR) of cerebral autoregulation model 124 classifying cerebral autoregulation status.

Receiver operating characteristic (ROC) curve 502A in graph 500A illustrates the classification results for a single subject (e.g., patient 101) from a test set using cerebral autoregulation model 124 trained using LSTM, such as the LSTM deep learning architecture 300 of FIG. 3. The area under ROC curve 502A, also referred to as AUROC, may equal to the probability that a classifier will rank a randomly chosen positive instance higher than a randomly chosen negative one, is 0.93. The accuracy of cerebral autoregulation model 124 trained using LSTM may be 0.72, the sensitivity of cerebral autoregulation model 124 trained using LSTM may be 0.95, and the specificity of cerebral autoregulation model 124 trained using LSTM may be 0.71.

Receiver operating characteristic (ROC) curve 502B in graph 500B illustrates the classification results for a single subject (e.g., patient 101) from a test set using cerebral autoregulation model 124 trained using CNN, such as the CNN deep learning architecture 400 of FIG. 4. The area under ROC curve 502B, also referred to as AUROC, may equal to the probability that a classifier will rank a randomly chosen positive instance higher than a randomly chosen negative one, is 0.97. The accuracy of cerebral autoregulation model 124 trained using CNN may be 0.93, the sensitivity of cerebral autoregulation model 124 trained using CNN may be 0.86, and the specificity of cerebral autoregulation model 124 trained using CNN may be 0.94.

Figure 6:
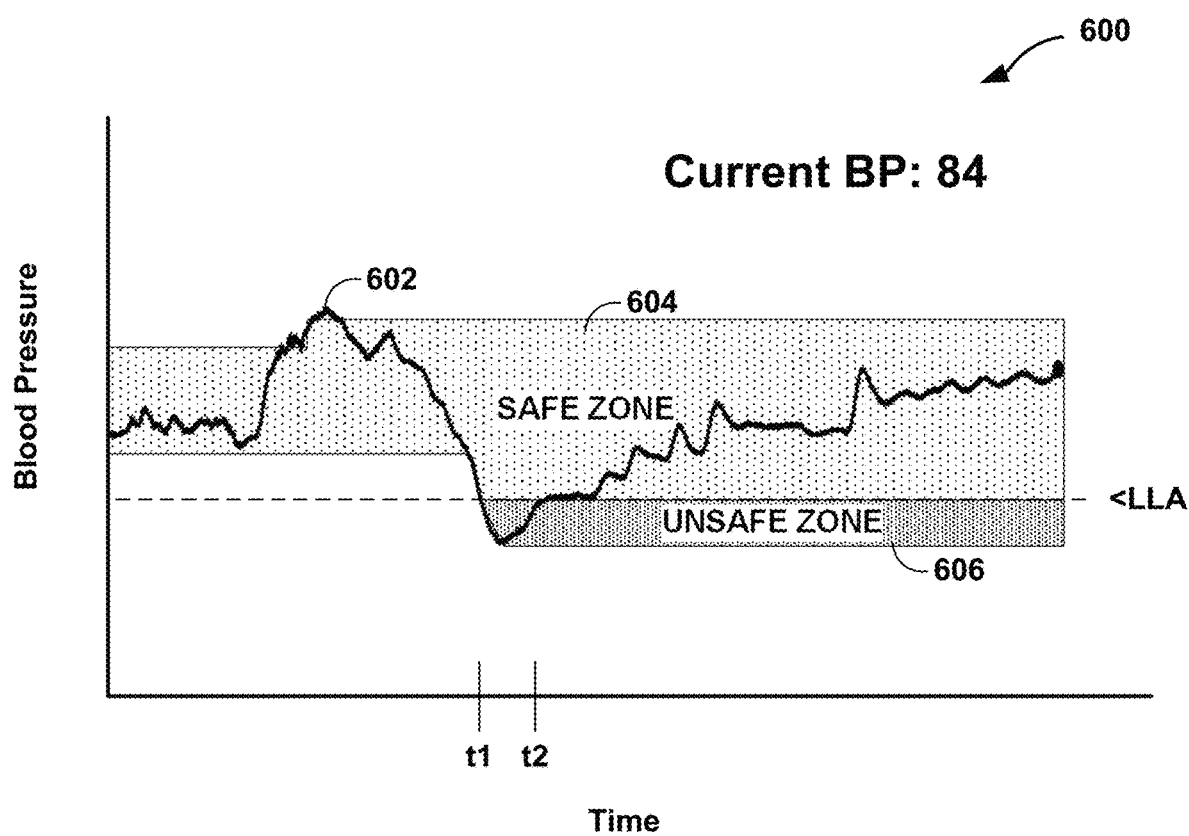
FIG. 6 illustrates example user interface that includes cerebral autoregulation information.

FIG. 6 illustrates example user interface that includes cerebral autoregulation information. As shown in FIG. 6, graphical user interface (GUI) 600 is an example of an interface that processing circuitry 110 of cerebral autoregulation monitoring system 100 may output for display at display 132 to provide the cerebral autoregulation status of patient 101. Graphical user interface 600 includes a graph of blood pressure value 602 of patient 101 over time.

Safe zone 604 in GUI 600 may illustrate a zone that is above the LLA, while unsafe zone 606 in GUI 600 may illustrate a zone that is below the LLA. GUI 600 illustrates the relationship between blood pressure value 602 of patient 101 and the cerebral autoregulation status of patient 101 by illustrating whether blood pressure value 602 of patient 101 is within safe zone 604 or unsafe zone 606. As illustrated in GUI 600, blood pressure value 602 is in safe zone 604 until blood pressure value 602 drops below the LLA to unsafe zone 606 at time t1, until the blood pressure value 602 returns to being above the LLA and therefore in safe zone 604 at time t2.

Figure 7:
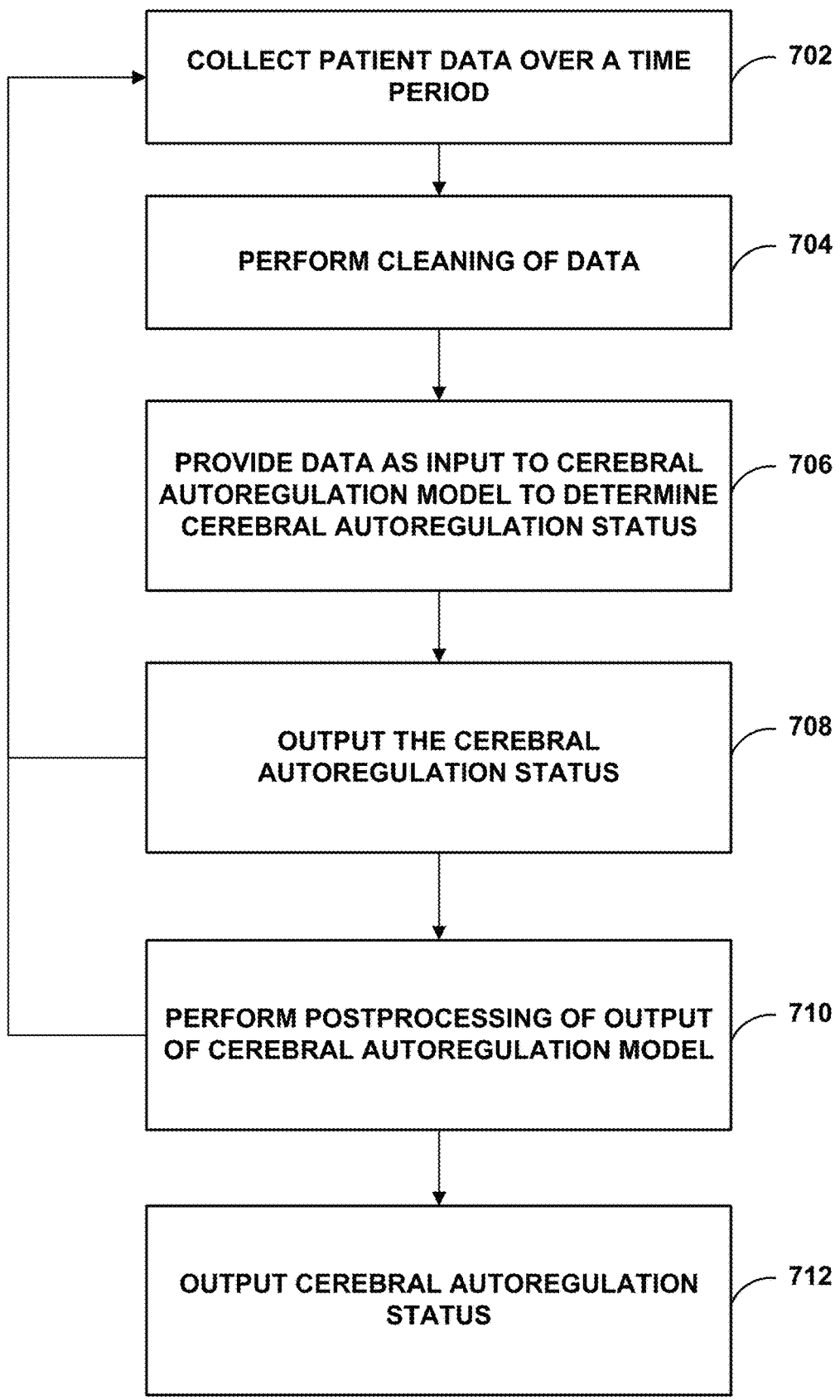
FIG. 7 is a flow diagram illustrating an example method for monitoring the cerebral autoregulation status of a patient.

FIG. 7 is a flow diagram illustrating an example method for monitoring the cerebral autoregulation status of a patient. Although FIG. 7 is described with respect to processing circuitry 110 of cerebral autoregulation monitoring system 100 (FIG. 1), in other examples, different processing circuitry, alone or in combination with processing circuitry 110, may perform any part of the technique of FIG. 7.

As shown in FIG. 7, the method includes processing circuitry 110 collecting patient data regarding patient 101 over a period of time (702). For example, the patient data may be collected over 30 seconds, 60 seconds, 90 seconds, 120 seconds, and the like. For example, if the period of time is 30 seconds, processing circuitry 110 may collect patient data starting from time t seconds to time t+30 seconds.

To collect the patient data, processing circuitry 110 may receive a blood pressure signal indicative of a blood pressure of patient 101, such as the MAP of patient 101, and an oxygen saturation signal indicative of a regional oxygen saturation of patient 101, such as the regional cerebral oxygen saturation of patient 101. For example, sensing devices 150 and 152 may generate the blood pressure signal and the oxygen saturation signal, which is received by processing circuitry 110, as discussed above.

In some examples, processing circuitry 110 performs cleaning of the collected patient data (704). For example, processing circuitry 110 may remove invalid value, such as values for any part of the data that are outside a range of valid values, performing smoothing of the data values, performing interpolation of the values, and the like.

Processing circuitry 110 provides the collected patient data, e.g., the patient data that has been cleaned, to cerebral autoregulation model 124 (706). In some examples, to provide the collected patient data to cerebral autoregulation model 124, processing circuitry 110 may provide the blood pressure (e.g., MAP) of patient 101 over the period of time and the regional cerebral oxygen saturation of patient 101 over at least the same period of time as inputs to cerebral autoregulation model 124. In some examples, if the regional cerebral oxygen saturation signal received by processing circuitry 110 includes two or more regional cerebral oxygen saturation values, processing circuitry 110 may separately provide each of the two or more regional cerebral oxygen saturation values as inputs to cerebral autoregulation model 124 or may provide an average of the two or more regional cerebral oxygen saturation values as input to cerebral autoregulation model 124.

In some examples, processing circuitry 110 may derive one or more values from the blood pressure of patient 101 over the period of time and the regional cerebral oxygen saturation of patient 101 over the period of time and may provide the derived one or more values as inputs to cerebral autoregulation model 124. For example, processing circuitry 110 may determine a gradient of the MAP of patient 101 over the period of time and may determine a gradient of the regional cerebral oxygen saturation of patient 101 over the period of time and may provide the determined gradients as inputs to cerebral autoregulation model 124.

In some examples, processing circuitry 110 may provide additional data associated with patient 101 as inputs to cerebral autoregulation model 124. For example, processing circuitry 110 may provide a bypass flag indicating whether patient 101 was undergoing a cardiopulmonary bypass procedure or another medical procedure during the period of time, morphology characteristics of the blood pressure and/or the regional cerebral oxygen saturation of patient 101 over the period of time (e.g., the raw blood pressure signals, the raw PPG signals, etc., including the peaks, locations, areas, etc. of the raw blood pressure signals and the raw PPG signals), the systolic and/or diastolic blood pressures of patient 101 of patient 101 over the period of time, demographic data of patient 101 such as height, weight, age, sex, disease state, and body mass index, and the like, as inputs to cerebral autoregulation model 124.

Processing circuitry 110 executes cerebral autoregulation model 124 to output, based on the inputted data, an indication of a cerebral autoregulation status of patient 101 (708). That is, processing circuitry 110 may use cerebral autoregulation model 124 to classify the cerebral autoregulation status of patient 101 as one of: intact, impaired, or unknown.

In some examples, cerebral autoregulation model 124 may determine, based on the inputted data, a confidence value associated with patient 101 being in an intact state and a confidence value associated with patient 101 being in an impaired state, and may, based on the determined confidence values, determine the cerebral autoregulation status of patient 101. For example, if cerebral autoregulation model 124 determines that the confidence value associated with patient 101 being in an intact state is higher than a confidence value associated with patient 101 being in an impaired state, then processing circuitry 110 determines, using model 124, that the cerebral autoregulation status of patient 101 is intact. Conversely, if cerebral autoregulation model 124 determines that the confidence value associated with patient 101 being in an impaired state is higher than a confidence value associated with patient 101 being in an intact state, then processing circuitry 110 determines, using model 124, that the cerebral autoregulation status of patient 101 is impaired.

In some examples, cerebral autoregulation model 124 determines a confidence difference threshold value. If cerebral autoregulation model 124 determines that the difference between the confidence value associated with patient 101 being in an impaired state and the confidence value associated with patient 101 being in an intact state is less than or equal to the confidence difference threshold value, then processing circuitry 110, using cerebral autoregulation model 124, may determine that the cerebral autoregulation status of patient 101 is unknown.

In some examples, cerebral autoregulation model 124 may average the currently determined confidence value associated with patient 101 being in an impaired state with previous confidence values associated with patient 101 being in an impaired state at the same blood pressure as the current blood pressure of patient 101 to determine the averaged confidence value associated with patient 101 being in an impaired state. Similarly, cerebral autoregulation model 124 may average the currently determined confidence value associated with patient 101 being in an intact state with previous confidence values associated with patient 101 being in an intact state at the same blood pressure as the current blood pressure of patient 101 to determine the averaged confidence value associated with patient 101 being in an intact state. Cerebral autoregulation model 124 may compare the averaged confidence value associated with patient 101 being in an intact state with the averaged confidence value associated with patient 101 being in an impaired state, such as by using the techniques described above, to determine the cerebral autoregulation status of patient 101.

In some examples, cerebral autoregulation model 124 may, in response to determining the confidence values associated with patient 101 being in an intact state and in an impaired state, log such confidence values in a confidence matrix stored in memory 120. The values in the confidence matrix may be used to compute the cerebral autoregulation status of patient 101 a posteriori.

Processing circuitry 110 may, in response to determining the cerebral autoregulation status of patient 101 also return to collect patient data regarding patient 101 over a period of time (702). In some examples, processing circuitry 110 may wait to reach the next second in time before returning to collect patient data regarding patient 101 over a period of time.

The method further includes processing circuitry 110, in response to determining the cerebral autoregulation status of patient 101, outputting an indication of the cerebral autoregulation status of patient 101, such as for display at display 132 (712). For example, processing circuitry 110 may output a graphical user interface, such as graphical user interface 600 of FIG. 6, which may provide the currently determined cerebral autoregulation status of patient 101 as well as additional information associated with patient 101, such as the blood pressure of patient 101, the regional cerebral oxygen saturation of patient 101, and the like.

Figure 8:
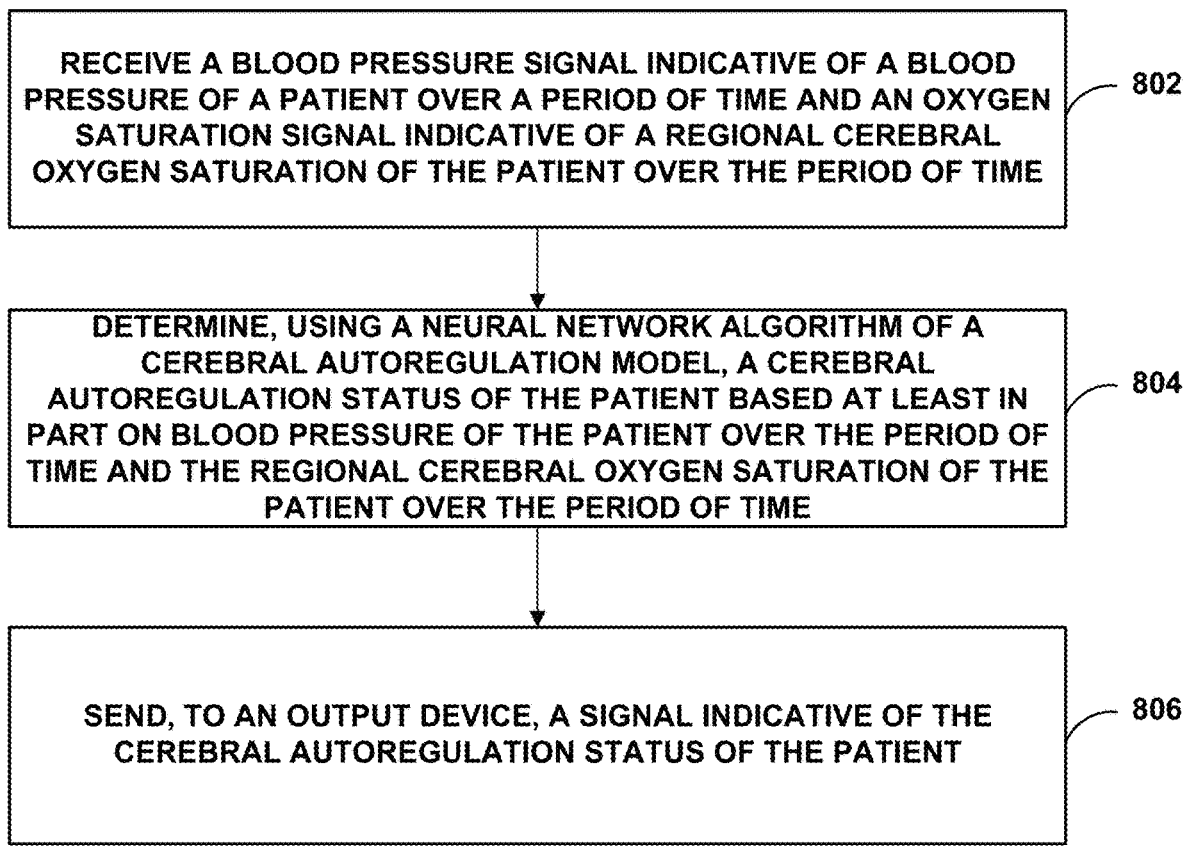
FIG. 8 is a flow diagram illustrating an example method for monitoring the cerebral autoregulation status of a patient.

FIG. 8 is a flow diagram illustrating an example method for monitoring the cerebral autoregulation status of a patient. Although FIG. 8 is described with respect to processing circuitry 110 of cerebral autoregulation monitoring system 100 (FIG. 1), in other examples, different processing circuitry, alone or in combination with processing circuitry 110, may perform any part of the technique of FIG. 8.

As shown in FIG. 8, processing circuitry 110 of cerebral autoregulation monitoring system 100 may receive a blood pressure signal indicative of a blood pressure of a patient 101 over a period of time and an oxygen saturation signal indicative of a regional cerebral oxygen saturation of the patient 101 over the period of time (802). Processing circuitry 110 may determine, using a neural network algorithm of a cerebral autoregulation model 124, a cerebral autoregulation status of the patient 101 based at least in part on blood pressure of the patient 101 over the period of time and the regional cerebral oxygen saturation of the patient 101 over the period of time (804). Processing circuitry 110 may send, to an output device, a signal indicative of the cerebral autoregulation status of the patient 101 (806).

In some examples, to determine, using the neural network algorithm of the cerebral autoregulation model 124, the cerebral autoregulation status of the patient 101 is further based at least in part on one or more of: a gradient of the blood pressure of the patient 101 over the period of time, a gradient of the regional cerebral oxygen saturation of the patient 101 over the period of time, a cerebral oxygenation index of the patient 101 over the period of time.

In some examples, the processing circuitry 110 is further configured to determine, using the neural network algorithm of the cerebral autoregulation model 124, the cerebral autoregulation status of the patient 101 based at least in part on a bypass flag indicating that the patient 101 was undergoing a cardiopulmonary bypass procedure during the period of time In some examples, the neural network algorithm is trained via machine learning over training data 214 to classify the cerebral autoregulation status of the patient 101 as one of: impaired, intact, or unknown.

In some examples, the training data 214 comprises two or more of: blood pressures of one or more patients over time, regional cerebral oxygen saturation values of the one or more patients over the time, gradients of the blood pressures of the one or more patients over each of a plurality of time periods, gradients of the regional cerebral oxygen saturations of the one or more patients over each of the plurality of time periods, cerebral oxygenation indices (COx) of the blood pressures and the regional cerebral oxygen saturations of the one or more patients over each of the time periods, one or more bypass flags indicating whether the one or more patients were undergoing a cardiopulmonary bypass procedure during each of the time periods, morphology characteristics of one or more of: the blood pressures or the regional cerebral oxygen saturations during each of the time periods, systolic blood pressures of the one or more patients over time, diastolic blood pressures of the one or more patients over time or demographic data associated with the one or more patients.

In some examples, the blood pressures of the one or more patients over time comprise, for each of the time periods, the blood pressures during the respective time period minus a mean of the blood pressures over time, and the regional cerebral oxygen saturations of the one or more patients over time comprise, for each of the time periods, the regional cerebral oxygen saturations during the respective time period minus a mean of the regional cerebral oxygen saturations over time.

In some examples, processing circuitry 110 may further be configured to determine, using the neural network algorithm of the cerebral autoregulation model 124, the cerebral autoregulation status of the patient 101 by at least: determining, a first confidence score associated with the cerebral autoregulation status of the patient 101 being intact, determining second confidence score associated with the cerebral autoregulation status of the patient 101 being impaired, and classifying the cerebral autoregulation status of the patient 101 as being one of: impaired, intact, or unknown based at least in part on comparing the first confidence score and the second confidence score.

In some examples, to classify the cerebral autoregulation status of the patient 101, the processing circuitry 101 is further configured to determine that a difference between the first confidence score and the second confidence score is within a confidence threshold, and in response to determining that the difference between the first confidence score and the second confidence score is less than or equal to a confidence threshold, classify the cerebral autoregulation status of the patient as being unknown.

In some examples, the processing circuitry 101 is further configured to determine an averaged first confidence score associated with the cerebral autoregulation status of the patient 101 being intact as an average of the first confidence score at a current blood pressure of the patient and a first set of previously determined confidence scores at the current blood pressure associated with the cerebral autoregulation status of the patient 101 being intact, determine an averaged second confidence score associated with the cerebral autoregulation status of the patient 101 being impaired as an average of the second confidence score at a current blood pressure of the patient and a second set of previously determined confidence scores at the current blood pressure associated with the cerebral autoregulation status of the patient 101 being impaired, and classify the cerebral autoregulation status of the patient 101 by comparing the averaged first confidence score and the averaged second confidence score to classify the cerebral autoregulation status of the patient 101 as being one of: impaired, intact, or unknown.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disk ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

The following clauses include example subject matter described herein.

Clause 1: A method includes receiving, by processing circuitry, a blood pressure signal indicative of a blood pressure of a patient over a period of time and an oxygen saturation signal indicative of a regional cerebral oxygen saturation of the patient over the period of time; determining, by the processing circuitry and using a neural network algorithm of a cerebral autoregulation model, a cerebral autoregulation status of the patient based at least in part on the blood pressure of the patient over the period of time and the regional cerebral oxygen saturation of the patient over the period of time; and sending, by the processing circuitry and to an output device, a signal indicative of the cerebral autoregulation status of the patient.

Clause 2: The method of clause 1, wherein determining, using the neural network algorithm of the cerebral autoregulation model, the cerebral autoregulation status of the patient further comprises determining, by the processing circuitry, the cerebral autoregulation status based at least in part on one or more of: a gradient of the blood pressure of the patient over the period of time; a gradient of the regional cerebral oxygen saturation of the patient over the period of time; or a cerebral oxygenation index of the patient over the period of time.

Clause 3: The method of clause 1 or 2, wherein determining, using the neural network algorithm of the cerebral autoregulation model, the cerebral autoregulation status of the patient further comprises determining, by the processing circuitry, the cerebral autoregulation status based at least in part on a bypass flag indicating that the patient was undergoing a cardiopulmonary bypass procedure during the period of time.

Clause 4: The method of any of clauses 1-3, wherein the neural network algorithm is trained via machine learning over training data to classify the cerebral autoregulation status of the patient as one of: impaired, intact, or unknown.

Clause 5: The method of clause 4, wherein the training data comprises two or more of: blood pressures of one or more patients over time; regional cerebral oxygen saturation values of the one or more patients over the time; gradients of the blood pressures of the one or more patients over each of a plurality of time periods; gradients of the regional cerebral oxygen saturation values of the one or more patients over each of the plurality of time periods; cerebral oxygenation indices (COx) determined based on the blood pressures and the regional cerebral oxygen saturations of the one or more patients over each of the time periods; one or more bypass flags indicating whether the one or more patients were undergoing a cardiopulmonary bypass procedure during each of the time periods; morphology characteristics of one or more of the blood pressures or the regional cerebral oxygen saturations during each of the time periods; systolic blood pressures of the one or more patients over time; diastolic blood pressures of the one or more patients over time; or demographic data associated with the one or more patients.

Clause 6: The method of clause 5, wherein: the blood pressures of the one or more patients over time comprise, for each of the time periods, the blood pressures during the respective time period minus a mean of the blood pressures over time; and the regional cerebral oxygen saturation values of the one or more patients over time comprise, for each of the time periods, the regional cerebral oxygen saturation values during the respective time period minus a mean of the regional cerebral oxygen saturation values over time.

Clause 7: The method of any of clauses 4-6, wherein determining, using the neural network algorithm of the cerebral autoregulation model, the cerebral autoregulation status of the patient further comprises: determining, by the processing circuitry, a first confidence score associated with the cerebral autoregulation status of the patient being intact; determining, by the processing circuitry, a second confidence score associated with the cerebral autoregulation status of the patient being impaired; and classifying, by the processing circuitry, the cerebral autoregulation status of the patient as being one of: impaired, intact, or unknown based at least in part on comparing the first confidence score and the second confidence score.

Clause 8: The method of clause 7, wherein classifying the cerebral autoregulation status of the patient further comprises: determining, by the processing circuitry, that a difference between the first confidence score and the second confidence score is within a confidence threshold; and in response to determining that the difference between the first confidence score and the second confidence score is less than or equal to a confidence threshold, classifying, by the processing circuitry, the cerebral autoregulation status of the patient as being unknown.

Clause 9: The method of clause 7 or 8, further includes determining, by the processing circuitry, an averaged first confidence score associated with the cerebral autoregulation status of the patient being intact as an average of the first confidence score at a current blood pressure of the patient and a first set of previously determined confidence scores at the current blood pressure associated with the cerebral autoregulation status of the patient being intact; determining an averaged second confidence score associated with the cerebral autoregulation status of the patient being impaired as an average of the second confidence score at a current blood pressure of the patient and a second set of previously determined confidence scores at the current blood pressure associated with the cerebral autoregulation status of the patient being impaired; and wherein classifying the cerebral autoregulation status of the patient further includes comparing, by the processing circuitry, the averaged first confidence score and the averaged second confidence score to classify the cerebral autoregulation status of the patient as being one of: impaired, intact, or unknown.

Clause 10: A system includes a blood pressure sensing device; an oxygen saturation sensing device; and processing circuitry configured to: receive a blood pressure signal indicative of a blood pressure of a patient over a period of time from the blood pressure sensing device and an oxygen saturation signal indicative of a regional cerebral oxygen saturation of the patient over the period of time from the oxygen saturation sensing device; determine, using a neural network algorithm of a cerebral autoregulation model, a cerebral autoregulation status of the patient based at least in part on blood pressure of the patient over the period of time and the regional cerebral oxygen saturation of the patient over the period of time; and send, to an output device, a signal indicative of the cerebral autoregulation status of the patient.

Clause 11: The system of clause 10, wherein to determine, using the neural network algorithm of the cerebral autoregulation model, the cerebral autoregulation status of the patient is further based at least in part on one or more of: a gradient of the blood pressure of the patient over the period of time; a gradient of the regional cerebral oxygen saturation of the patient over the period of time; or a cerebral oxygenation index of the patient over the period of time.

Clause 12: The system of clause 10 or 11, wherein the processing circuitry is further configured to determine, using the neural network algorithm of the cerebral autoregulation model, the cerebral autoregulation status of the patient based at least in part on a bypass flag indicating that the patient was undergoing a cardiopulmonary bypass procedure during the period of time.

Clause 13: The system of any of clauses 10-12, wherein the neural network algorithm is trained via machine learning over training data to classify the cerebral autoregulation status of the patient as one of: impaired, intact, or unknown.

Clause 14: The system of clause 13, wherein the training data comprises two or more of: blood pressures of one or more patients over time; regional cerebral oxygen saturation values of the one or more patients over the time; gradients of the blood pressures of the one or more patients over each of a plurality of time periods; gradients of the regional cerebral oxygen saturations of the one or more patients over each of the plurality of time periods; cerebral oximetry indices (COx) of the blood pressures and the regional cerebral oxygen saturations of the one or more patients over each of the time periods; one or more bypass flags indicating whether the one or more patients were undergoing a cardiopulmonary bypass procedure during each of the time periods; morphology characteristics of one or more of: the blood pressures or the regional cerebral oxygen saturations during each of the time periods; systolic blood pressures of the one or more patients over time; diastolic blood pressures of the one or more patients over time; or demographic data associated with the one or more patients.

Clause 15: The system of clause 14, wherein: the blood pressures of the one or more patients over time comprise, for each of the time periods, the blood pressures during the respective time period minus a mean of the blood pressures over time; and the regional cerebral oxygen saturations of the one or more patients over time comprise, for each of the time periods, the regional cerebral oxygen saturations during the respective time period minus a mean of the regional cerebral oxygen saturations over time.

Clause 16: The system of any of clauses 13-15, wherein the processing circuitry is configured to determine, using the neural network algorithm of the cerebral autoregulation model, the cerebral autoregulation status of the patient by at least: determine a first confidence score associated with the cerebral autoregulation status of the patient being intact; determine a second confidence score associated with the cerebral autoregulation status of the patient being impaired; and classify the cerebral autoregulation status of the patient as being one of: impaired, intact, or unknown based at least in part on comparing the first confidence score and the second confidence score.

Clause 17: The system of clause 16, wherein to classify the cerebral autoregulation status of the patient, the processing circuitry is further configured to: determine that a difference between the first confidence score and the second confidence score is within a confidence threshold; and in response to determining that the difference between the first confidence score and the second confidence score is less than or equal to a confidence threshold, classify the cerebral autoregulation status of the patient as being unknown.

Clause 18: The system of clause 16 or 17, wherein the processing circuitry is further configured to: determine an averaged first confidence score associated with the cerebral autoregulation status of the patient being intact as an average of the first confidence score at a current blood pressure of the patient and a first set of previously determined confidence scores at the current blood pressure associated with the cerebral autoregulation status of the patient being intact; determine an averaged second confidence score associated with the cerebral autoregulation status of the patient being impaired as an average of the second confidence score at a current blood pressure of the patient and a second set of previously determined confidence scores at the current blood pressure associated with the cerebral autoregulation status of the patient being impaired; and classify the cerebral autoregulation status of the patient by comparing the averaged first confidence score and the averaged second confidence score to classify the cerebral autoregulation status of the patient as being one of: impaired, intact, or unknown.

Clause 19: A non-transitory computer readable storable medium includes receive a blood pressure signal indicative of a blood pressure of a patient over a period of time and an oxygen saturation signal indicative of a regional cerebral oxygen saturation of the patient over the period of time; determine, using a neural network algorithm of a cerebral autoregulation model, a cerebral autoregulation status of the patient based at least in part on blood pressure of the patient over the period of time and the regional cerebral oxygen saturation of the patient over the period of time; and send, to an output device, a signal indicative of the cerebral autoregulation status of the patient.

Clause 20: The non-transitory computer readable storable medium of clause 19, wherein the instructions that cause the processing circuitry to determine, using the neural network algorithm of the cerebral autoregulation model, the cerebral autoregulation status of the patient further causes the processing circuitry to: determine, a first confidence score associated with the cerebral autoregulation status of the patient being intact; determine second confidence score associated with the cerebral autoregulation status of the patient being impaired; and classify the cerebral autoregulation status of the patient as being one of: impaired, intact, or unknown based at least in part on comparing the first confidence score and the second confidence score.

Various examples of the disclosure have been described. Any combination of the described systems, operations, or functions is contemplated. These and other examples are within the scope of the following claims.

What is claimed is:

1. A method comprising:
receiving, by processing circuitry, a blood pressure signal indicative of a blood pressure of a patient over a period of time and an oxygen saturation signal indicative of a regional cerebral oxygen saturation of the patient over the period of time;
determining, by the processing circuitry and using a neural network algorithm of a cerebral autoregulation model, a cerebral autoregulation status of the patient based at least in part on the blood pressure of the patient over the period of time and the regional cerebral oxygen saturation of the patient over the period of time, wherein the neural network algorithm is trained via machine learning over training data to classify the cerebral autoregulation status of the patient as one of impaired, intact, or unknown based at least in part on comparing a first confidence score associated with the cerebral autoregulation status of the patient being intact with a second confidence score associated with the cerebral autoregulation status of the patient being impaired; and
sending, by the processing circuitry and to an output device, a signal indicative of the cerebral autoregulation status of the patient.

2. The method of claim 1, wherein determining, using the neural network algorithm of the cerebral autoregulation model, the cerebral autoregulation status of the patient further comprises determining, by the processing circuitry, the cerebral autoregulation status based at least in part on one or more of:
a gradient of the blood pressure of the patient over the period of time;
a gradient of the regional cerebral oxygen saturation of the patient over the period of time; or
a cerebral oxygenation index of the patient over the period of time.

3. The method of claim 1, wherein determining, using the neural network algorithm of the cerebral autoregulation model, the cerebral autoregulation status of the patient further comprises determining, by the processing circuitry, the cerebral autoregulation status based at least in part on a bypass flag indicating that the patient was undergoing a cardiopulmonary bypass procedure during the period of time.

4. The method of claim 1, wherein the training data comprises two or more of:
blood pressures of one or more patients over time;
regional cerebral oxygen saturation values of the one or more patients over the time;
gradients of the blood pressures of the one or more patients over each time period of a plurality of time periods;
gradients of the regional cerebral oxygen saturation values of the one or more patients over each time period of the plurality of time periods;
cerebral oxygenation indices (COx) determined based on the blood pressures and the regional cerebral oxygen saturation values of the one or more patients over each time period of the plurality of time periods;
one or more bypass flags indicating whether the one or more patients were undergoing a cardiopulmonary bypass procedure during each time period of the plurality of time periods;
morphology characteristics of one or more of the blood pressures or the regional cerebral oxygen saturation values during each time period of the plurality of time periods;
systolic blood pressures of the one or more patients over time;
diastolic blood pressures of the one or more patients over time; or
demographic data associated with the one or more patients.

5. The method of claim 4, wherein:
the blood pressures of the one or more patients over time comprise, for each time period of the plurality of time periods, the blood pressures during the respective time period minus a mean of the blood pressures over time; and
the regional cerebral oxygen saturation values of the one or more patients over time comprise, for each time period of the plurality of time periods, the regional cerebral oxygen saturation values during the respective time period minus a mean of the regional cerebral oxygen saturation values over time.

6. The method of claim 1, wherein determining, using the neural network algorithm of the cerebral autoregulation model, the cerebral autoregulation status of the patient further comprises:

determining, by the processing circuitry, the first confidence score associated with the cerebral autoregulation status of the patient being intact; and determining, by the processing circuitry, the second confidence score associated with the cerebral autoregulation status of the patient being impaired.

7. The method of claim 6, further comprising:

determining, by the processing circuitry, an averaged first confidence score associated with the cerebral autoregulation status of the patient being intact as an average of the first confidence score at a current blood pressure of the patient and a first set of previously determined confidence scores at the current blood pressure associated with the cerebral autoregulation status of the patient being intact;

determining an averaged second confidence score associated with the cerebral autoregulation status of the patient being impaired as an average of the second confidence score at a current blood pressure of the patient and a second set of previously determined confidence scores at the current blood pressure associated with the cerebral autoregulation status of the patient being impaired; and wherein determining the cerebral autoregulation status of the patient further includes comparing, by the processing circuitry, the averaged first confidence score and the averaged second confidence score to classify the cerebral autoregulation status of the patient as being one of: impaired, intact, or unknown.

8. The method of claim 1, wherein determining, using the neural network algorithm, the cerebral autoregulation status of the patient comprises:

determining, by the processing circuitry, that a difference between the first confidence score and the second confidence score is within a confidence threshold; and in response to determining that the difference between the first confidence score and the second confidence score is less than or equal to a confidence threshold, classifying, by the processing circuitry, the cerebral autoregulation status of the patient as being unknown.

9. A system comprising:

a blood pressure sensing device;

an oxygen saturation sensing device; and processing circuitry configured to:

receive a blood pressure signal indicative of a blood pressure of a patient over a period of time from the blood pressure sensing device and an oxygen saturation signal indicative of a regional cerebral oxygen saturation of the patient over the period of time from the oxygen saturation sensing device;

determine, using a neural network algorithm of a cerebral autoregulation model, a cerebral autoregulation status of the patient based at least in part on blood pressure of the patient over the period of time and the regional cerebral oxygen saturation of the patient over the period of time, wherein the neural network algorithm is trained via machine learning over training data to classify the cerebral autoregulation status of the patient as one of impaired, intact, or unknown based at least in part on comparing a first confidence score associated with the cerebral autoregulation status of the patient being intact with a second confidence score associated with the cerebral autoregulation status of the patient being impaired; and send, to an output device, a signal indicative of the cerebral autoregulation status of the patient.

10. The system of claim 9, wherein to determine, using the neural network algorithm of the cerebral autoregulation model, the cerebral autoregulation status of the patient is further based at least in part on one or more of:

a gradient of the blood pressure of the patient over the period of time;

a gradient of the regional cerebral oxygen saturation of the patient over the period of time; or a cerebral oxygenation index of the patient over the period of time.

11. The system of claim 9, wherein the processing circuitry is further configured to determine, using the neural network algorithm of the cerebral autoregulation model, the cerebral autoregulation status of the patient based at least in part on a bypass flag indicating that the patient was undergoing a cardiopulmonary bypass procedure during the period of time.

12. The system of claim 10, wherein the training data comprises two or more of:

blood pressures of one or more patients over time;

regional cerebral oxygen saturation values of the one or more patients over the time;

gradients of the blood pressures of the one or more patients over each time period of a plurality of time periods;

gradients of the regional cerebral oxygen saturation values of the one or more patients over each time period of the plurality of time periods;

cerebral oximetry indices (COx) of the blood pressures and the regional cerebral oxygen saturation values of the one or more patients over each time period of the plurality of time periods;

one or more bypass flags indicating whether the one or more patients were undergoing a cardiopulmonary bypass procedure during each time period of the plurality of time periods;

morphology characteristics of one or more of: the blood pressures or the regional cerebral oxygen saturation values during each time period of the plurality of time periods;

systolic blood pressures of the one or more patients over time;

diastolic blood pressures of the one or more patients over time; or demographic data associated with the one or more patients.

13. The system of claim 12, wherein:

the blood pressures of the one or more patients over time comprise, for each of the time periods, the blood pressures during the respective time period minus a mean of the blood pressures over time; and the regional cerebral oxygen saturation values of the one or more patients over time comprise, for each of the time periods, the regional cerebral oxygen values during the respective time period minus a mean of the regional cerebral oxygen saturation values over time.

14. The system of claim 10, wherein to determine, using the neural network algorithm of the cerebral autoregulation model, the cerebral autoregulation status of the patient, the processing circuitry is further configured to:

determine the first confidence score associated with the cerebral autoregulation status of the patient being intact; and determine the second confidence score associated with the cerebral autoregulation status of the patient being impaired.

15. The system of claim 14, wherein to determine, using the neural network algorithm, the cerebral autoregulation status of the patient, the processing circuitry is further configured to:
  determine that a difference between the first confidence score and the second confidence score is within a confidence threshold; and
  in response to determining that the difference between the first confidence score and the second confidence score is less than or equal to a confidence threshold, classify the cerebral autoregulation status of the patient as being unknown.

16. The system of claim 14, wherein the processing circuitry is further configured to:
  determine an averaged first confidence score associated with the cerebral autoregulation status of the patient being intact as an average of the first confidence score at a current blood pressure of the patient and a first set of previously determined confidence scores at the current blood pressure associated with the cerebral autoregulation status of the patient being intact;
  determine an averaged second confidence score associated with the cerebral autoregulation status of the patient being impaired as an average of the second confidence score at a current blood pressure of the patient and a second set of previously determined confidence scores at the current blood pressure associated with the cerebral autoregulation status of the patient being impaired; and
  determine the cerebral autoregulation status of the patient by comparing the averaged first confidence score and the averaged second confidence score to classify the cerebral autoregulation status of the patient as being one of: impaired, intact, or unknown.

17. A non-transitory computer readable storable medium comprising instructions that, when executed, cause processing circuitry to:
  receive a blood pressure signal indicative of a blood pressure of a patient over a period of time and an oxygen saturation signal indicative of a regional cerebral oxygen saturation of the patient over the period of time;
  determine, using a neural network algorithm of a cerebral autoregulation model, a cerebral autoregulation status of the patient based at least in part on blood pressure of the patient over the period of time and the regional cerebral oxygen saturation of the patient over the period of time, wherein the neural network algorithm is trained via machine learning over training data to classify the cerebral autoregulation status of the patient as one of impaired, intact, or unknown based at least in part on comparing a first confidence score associated with the cerebral autoregulation status of the patient being intact with a second confidence score associated with the cerebral autoregulation status of the patient being impaired; and
  send, to an output device, a signal indicative of the cerebral autoregulation status of the patient.

18. The non-transitory computer readable storable medium of claim 17, wherein the instructions that cause the processing circuitry to determine, using the neural network algorithm of the cerebral autoregulation model, the cerebral autoregulation status of the patient further causes the processing circuitry to:
  determine, a first confidence score associated with the cerebral autoregulation status of the patient being intact;
  determine second confidence score associated with the cerebral autoregulation status of the patient being impaired; and
  determine the cerebral autoregulation status of the patient as being one of: impaired, intact, or unknown based at least in part on comparing the first confidence score and the second confidence score.

* * * * *